US007501129B2

(12) United States Patent
Williams et al.

(10) Patent No.: US 7,501,129 B2
(45) Date of Patent: Mar. 10, 2009

(54) VECTORS COMPRISING GUINEA PIG CMV REGULATORY ELEMENTS

(75) Inventors: Steven Geraint Williams, Cheshire (GB); Alistair Simpson Irvine, Derbyshire (GB); Jonathan Gawn, Cheshire (GB)

(73) Assignee: Millipore Corporation, Billerica, MA (US)

( * ) Notice: Subject to any disclaimer, the term of this patent is extended or adjusted under 35 U.S.C. 154(b) by 165 days.

(21) Appl. No.: 11/368,139

(22) Filed: Mar. 3, 2006

(65) Prior Publication Data

US 2006/0223772 A1    Oct. 5, 2006

Related U.S. Application Data

(60) Provisional application No. 60/661,553, filed on Mar. 14, 2005.

(30) Foreign Application Priority Data

Mar. 5, 2005    (GB) ................. 0504587.7

(51) Int. Cl.
*A61K 39/25*    (2006.01)
*A61K 39/12*    (2006.01)
*C12P 19/34*    (2006.01)
*C12N 5/06*    (2006.01)

(52) U.S. Cl. ............... 424/230.1; 435/91.1; 435/91.32; 435/91.33; 435/326; 435/333; 424/186.1

(58) Field of Classification Search ............. None
See application file for complete search history.

(56) References Cited

U.S. PATENT DOCUMENTS

| 4,968,615 | A | 11/1990 | Koszinowski et al. |
| 5,168,062 | A | 12/1992 | Stinski |
| 5,591,639 | A | 1/1997 | Bebbington |

FOREIGN PATENT DOCUMENTS

| WO | WO-00/05393 A2 | 2/2000 |
| WO | WO-02/081677 A | 10/2002 |
| WO | WO-02/099089 A1 | 12/2002 |

OTHER PUBLICATIONS

Yin, Chaoying, Ph.D., "Guinea Pig Cytomegalovirus Immediate Early Gene Expression," A Thesis in Microbiology and Immunology, The Pennsylvania State University, Aug. 1991, pp. 1-192.
Yin, Chaoying et al., "Guinea Pig Cytomegalovirus Immediate-Early Transcription," Dept. of Microbiology and Immunology, The Pennsylvania State University C ollege of Medicine, Journal of Virology, Apr. 1990, p. 1537-1548, vol. 64, No. 4.
Thomsen, Darrell R. et al., "Promoter-Regulatory Region Of The Major Immediate Early Gene Of Human Cytomegalovirus," Dept. of Microbiology, School of Medicine, University of Iowa, Proc. Natl. Acad. Sci., USA, vol. 81, pp. 659-663, Feb. 1984.
Isomura, Hiroki et al., "The Human Cytomegalovirus Major Immediate-Early Enhancer Determines the Efficiency Of Immediate-Early Gene Transcription and Viral Replication in Permissive Cells at Low Multiplicity of Infection," Dept. of Microbiology, Carver College of Medicine, University of Iowa, Journal Of Virology, Mar. 2003, pp. 3602-3614, vol. 77, No. 6.
Isom, Harriet C., "Characterization of Guinea Pig Cytomegalovirus DNA," Dep. of Microbiology and Cancer Research Center, The Pennsylvania State University College of Medicine, Journal Of Virology, Feb. 1984, pp. 426-436, vol. 49, No. 2.
Gao, Min et al., "Characterization Of The Guinea Pig Cytomegalovirus Genome by Molecular Cloning And Physical Mapping," Dept. of Microbiology and Cancer Research Center, The Pennsylvania State University College of Medicine, Journal Of Virology, Nov. 1984, pp. 436-447, vol. 52, No. 2.
Kadonaga, James T., "Regulation of RNA Polymerase II Transcription By Sequence-Specific DNA Binding Factors," Review, Section of Molecular Biology, 0347, University of California, Cell, vol. 116, pp. 247-257, Jan. 23, 2004.
Antequera, Francisco, et al., "Number of GpG Islands And Genes In Human And Mouse," Institute of Cell and Molecular Biology, University of Edinburgh, Proc. Natl. Acad. Sci. USA, vol. 90, pp. 11995-11999, Dec. 1993, Genetics.
Castillo, Jonathan P. et al., "Human Cytomegalovirus Immediate Early Proteins And Cell Growth Control," University of Massachusetts Medical school, Gene 290 (2002), pp. 19-34.
Dorsch-Hasler, Karoline, et al., "A Long And Complex Enhancer Activates Transcription Of The Gene Coding For The Highly Abundant Immediate Early mRNA in Murine Cytomegalovirus," Proc. Natl. Acad. Sci. USA, vol. 82, pp. 8325-8329, Dec. 1985, Biochemistry.
PCT International Search Report for PCT/GB2006/000802, 6 pages.

*Primary Examiner*—Bruce Campell
*Assistant Examiner*—Sharon Hurt

(57) ABSTRACT

The invention comprises novel polynucleotides, and related vectors, host cells, methods, and compositions, containing transcriptional enhancers providing very high levels of expression of operably-linked expressible nucleic acid sequences in eukaryotic cells. Advantageously the enhancers may be used in combination with their naturally-associated promoters and/or other genetic elements that increase transcription. The invention comprises eukaryotic expression vectors that are capable of providing increased levels of expression in many cell types over that obtainable from human or murine CMV IE enhancer/promoter elements.

18 Claims, 7 Drawing Sheets

Figure 1

```
                AP1                          NFκB
     ttagtcatatgttacttggcagaggccgcatggaaagtccctggacgtgg    50
                                     SRF
     gacatctgattaatacgtgaggaggtcagccatgttctttttggcaaagg   100 actacggtcattggacgtttgattggcatgggatagggtcagccagagtt   150
           SRF                NFκB
     aacagtgttctttttggcaaagggatacgtggaaagtcccgggccattac    200
                                              AP1
     agtaaactgatacggggacaaagcacagccatatttagtcatgtattgct   250
            NFκB
     tggcagagggtctatggaaagtccctggacgtgggacgtctgattaatat   300
                                        SRF
     gaaagaaggtcagccagaggtagctgtgtcctttttggcaaagggatacg   350 gttatgggacgtttgattggactgggatagggtcagccagagttaacagt   400
          SRF           NFκB
     gttctttttggcaaaggaaacgtggaaagtcccgggccatttacagtaaac   450
                                 AP1         SRF
     tgatactgggacaaagtacacccatatttagtcatgttctttttggcaaa   500
             NFκB              GCN4
     gagcatctggaaagtcccgggcagcattatagtcacttggcagagggaaa   550 gggtcactcagagttaagtacatctttccagggccaatattccagtaaat   600
                  AP1                  NFκB
     tacacttagttttatgcaaatcagccacaaaggggatttttcccggtcaat   650
       GCN4        AP1        CAAT box
     tatgacttttttccttagtcatgcggtatccaattactgccaaattggcag   700
                    GCN4              NFκB
     tacatactaggtgattcactgacatttggccgtcctctggaaagtccctg   750
                         GCN4
     gaaaccgctcaagtactgtatcatggtgactttgcattttttggagagcac   800 gccccactccaccattggtccacgtaccctatgggggagtggtttatgag   850
      TATA Box         CRS
     tatataagggctccggtttagaagccgggcagagcg                  887
```

VECTORS COMPRISING GUINEA PIG CMV REGULATORY ELEMENTS

CROSS-REFERENCE TO RELATED APPLICATIONS

This application claims priority based on GB Patent Application GB0504587.7, filed Mar. 5, 2005, and U.S. Provisional Patent Application No. 60/661,553, filed Mar. 14, 2005, each of which is hereby incorporated by reference in full.

FIELD OF THE INVENTION

The invention relates to the field of recombinant DNA technology and, in particular, the development of vectors for the expression of recombinant proteins.

BACKGROUND

Expression of heterologous genes in eukaryotic cells is a fundamental aspect of biotechnology with many academic and commercial applications. Expression of such genes requires transcription by RNA polymerase II (Pol II), which is driven by cis-acting genetic elements known as promoters and enhancers.

In simple terms, promoters are directional elements that act to initiate transcription of sequences situated less than 100 (and usually less than 50) nucleotide base pairs (bp) downstream. They contain a number of short consensus nucleotide sequences that act as binding sites for various proteins that participate in the initiation of transcription and the assembly of a multi-subunit complex known as the pre-initiation complex (McKnight and Tjian, 1987, Cell 46: 795-805). In most genes, this occurs at a very widely conserved sequence known as the TATA box (TATAAA) to which the TATA box-binding protein (TBP, a subunit of the general transcription factor TFIID) binds. There follows an ordered assembly of more than ten further transcription factors to finally form the Pol II holoenzyme complex. RNA transcription actually starts at an initiator site about 25-30 bases downstream (Breathnach and Chambon, 1981, Annu Rev Biochem 50: 349-393) to which TBP also binds.

Most functional promoters contain further upstream promoter elements (UPEs), of which the most highly conserved are the CAAT box (CCAAT, the binding site for the transcription factors CBF, C/EBP and NF-1), about 70-200 bp upstream, and the GC box (GGGCGG, binding site for the general transcription factor Sp-1) a similar distance upstream. Although basal levels of transcription occur from the TATA box alone, for most promoters at least the CAAT and GC boxes are required for optimal levels of transcription.

Enhancers are sequences that act non-directionally to increase transcription from promoters situated locally but not necessarily immediately adjacent (up to several kilobases away (Kadonaga (2004) Cell 116: 247-257). Enhancers contain short (8-12 bp) consensus sequences representing the binding sites for a wide range of transcriptional activator proteins (Ondek et al, 1988, Science 236: 1237-1244) including some, such as NF-1 and SP-1 that are also associated with promoter elements. These sequences are often duplicated in tandem or inverted repeats.

In some natural transcription units, including the very active immediate/early gene transcription units of many DNA viruses such as cytomegalovirus, enhancer and promoter elements may be functionally combined into what is effectively one extended upstream element.

Promoters may be regulated, being responsive to cell type, temperature, metal ions or other factors; or constitutive, giving transcription that is unresponsive to such factors. For many purposes a strong, constitutive promoter giving consistent, high, levels of transcription in many, if not all, cell types is highly advantageous. For many years the enhancer/promoter element driving immediate/early gene expression in human cytomegalovirus has been very widely used for driving such expression of heterologous genes in eukaryotic expression vectors (Foecking & Hoffstetter, 1986, Gene 45: 101-105).

Human cytomegalovirus (CMV) is a member of the beta-herpesvirus family and is responsible for gastrointestinal and respiratory infections, hepatitis, and retinitis. As with other herpesviruses, CMV can persist in latent infections and can be reactivated in immunocompromised individuals. In cell culture, human CMV replicates productively in terminally differentiated cells such as fibroblast, epithelial, and endothelial cells and in monocyte-derived macrophages (Isomura and Stinski, 2003, J Virol 77: 3602-3614 and references therein).

During productive infection, there is an ordered expression of sets of CMV genes, designated immediate-early (IE), early, or late. The human CMV IE genes are thought to play a critical role in the efficiency of replication (reviewed in Castillo and Kowalik, 2002, Gene 290: 19-34).

The region upstream of the human CMV IE promoter is divided into three regions, the modulator, the unique region, and the enhancer. The enhancer is also divided into a distal and a proximal enhancer. The distal enhancer is necessary for efficient IE gene expression and viral replication at a low MOI. Human CMVs have very strong enhancers for the expression of IE genes. The human CMV enhancer has four 18-bp repeat elements containing an NF-κB or rel binding site, five 19-bp repeat elements containing a CREB or ATF binding site, two AP-1 binding sites, and multiple SP-1 sites (Thomsen et al, 1984, Proc Natl Acad Sci USA 81: 659-663; Meier and Stinski, 1996, Intervirology 39: 331-342). The murine CMV enhancer contains six NF-κB or rel binding sites, one CREB or ATF binding site, and at least seven AP-1 binding sites (Dorsch-Hasler et al, 1985, Proc Natl Acad Sci USA 82: 8325-8329). The different cis-acting elements act individually and synergistically to stabilize the RNA polymerase II transcription initiation complex on the promoter.

A number of cytomegaloviruses predominantly infecting other host species are known, although, in many cases, the exact taxonomy and degree of cross-species relatedness is provisional. Cytomegalovirus-like viruses infecting a number of primate species (including African green monkey, Rhesus monkey and bonobo) and rodents including mouse, rat and guinea pig are recognised. Of these, only the murine and rat promoter-enhancers have been subject to detailed functional analysis. Comparison of these species with human CMV shows that the functions of the IE promoter-enhancers are not directly comparable, probably because of the presence of unrecognised cis-acting elements contributing to downstream transcription in cells of different species (Isomura and Stinski, 2003, J Virol 77: 3602-3614).

However, both human and murine CMV IE promoter-enhancers produce high levels of constitutive expression of heterologous genes in eukaryotic expression vectors and are widely used in biotechnology. Such use of the human CMV promoter was disclosed in U.S. Pat. No. 5,168, 062 (Stinski/University of Iowa). Use of the promoter, enhancer and functionally complete 5' (upstream) untranslated region including the first intron of the human cytomegalovirus major immediate-early gene, wherein this is not directly linked to its natural DNA coding sequence is claimed by U.S. Pat. No. 5,591,639 (Bebbington/Celltech). Use of the murine CMV IE enhancer is disclosed by U.S. Pat. No. 4,968,615 (Koszinowski et al)

Guinea pig CMV (GPCMV) produces a disease of guinea pigs with many similarities to the pathology of human CMV infections. Attempts to characterise the genome (Isom et al, 1984, J Virology 49: 426-436; Gao and Isom, 1984, J Virology 52: 436-447) suggested that the structural organisation of the genome was unique amongst herpesviruses. Although of a similar size to human and murine CMV, the GPCMV genome was far simpler than that of human CMV and most closely resembled that of murine CMV. However, the GPCMV genome had several unusual features, particularly in the structure of the terminal regions. Later studies of IE gene expression identified an IE region by sequence comparison with human CMV (Yin et al, 1990, J Virol 64: 1537-1548) and the expression and processing of IE transcripts was analysed. However, there was no analysis of the usefulness of the IE promoter-enhancer for the expression of heterologous genes.

The sequence of the 'HRv' (Hind III-EcoRV) immediate-early upstream fragment of the GPCMV genome, containing the 5' end of IE1 coding sequence and the upstream promoter/enhancer regions was sequenced (Yin, 1991, *Guinea pig cytomegalovirus immediate-early gene expression,* PhD thesis, Pennsylvania State University, USA) and shown to contain a region of repetitive sequences, typical of a CMV IE regulatory region. Three short repeats, GP-1, GP-2 and GP-3 were identified. GP-1 is an 18-bp repeat occurring 9 times (73-100% similarity to a GGCCCGGGACTTTCCA consensus) containing an NF-κB binding site and corresponding to the HCMV 18-bp repeat. GP-2 is a 17-bp repeat occurring 10 times (86-100% similarity to a TGTCCTTTTTGGCAAA consensus) and containing a core sequence similar to the consensus SRE (serum response element). GP-3 is repeated 4 times in the proximal upstream region and contains GTGACTTT, a sequence identified as a binding site for c-jun or GCN4 (Hill et al, 1984, Science 234: 451-457).

Although this work suggested that the GPCMV IE upstream region contained a strong promoter, due to the way the reporter constructs were made certain artefacts could not be excluded. Firstly, the HRv fragment also appears to include the first exon and part of the first intron of the IE1 gene. This intron contains three copies of a putative NF-1 binding site, which may have artificially boosted the apparent strength of the promoter. Secondly, the reporter constructs used to test the GPCMV fragments contained an SV40 promoter (itself a strong viral promoter), so that reporter expression resulted from the effect of a double GPCMV/SV40 promoter. As a result it is not possible to make comparisons of the GPCMV enhancer/promoter alone with other strong promoters generally, or even with other CMV IE enhancer/promoters.

The applicant's co-pending patent application PCT/GB99/02357 (WO 00/05393), incorporated by reference herein, describes elements that are responsible, in their natural chromosomal context, for establishing an open chromatin structure across a locus that consists exclusively of ubiquitously expressed, housekeeping genes. These elements are not derived from a Locus Control Region (LCR) and comprise extended methylation-free CpG islands. The term Ubiquitous Chromatin Opening Element (UCOE) has been used to describe such elements.

In mammalian DNA, the dinucleotide CpG is recognised by a DNA methyltransferase enzyme that methylates cytosine to 5-methylcytosine. However, 5-methylcytosine is unstable and is converted to thymine. As a result, CpG dinucleotides occur far less frequently than one would expect by chance. Some sections of genomic DNA nevertheless do have a frequency of CpG that is closer to that expected, and these sequences are known as "CpG islands". As used herein a "CpG island" is defined as a sequence of DNA, of at least 200 bp, that has a GC content of at least 50% and an observed/expected CpG content ratio of at least 0.6 (i.e. a CpG dinucleotide content of at least 60% of that which would be expected by chance) (Gardiner-Green M and Frommer M. *J Mol Biol* 196, 261-282 (1987); Rice P, Longden I and Bleasby A *Trends Genet* 16, 276-277 (2000).

Methylation-free CpG islands are well-known in the art (Bird et al (1985) Cell 40: 91-99, Tazi and Bird (1990) Cell 60: 909-920) and may be defined as CpG islands where a substantial proportion of the cytosine residues are not methylated and which usually extend over the 5' ends of two closely spaced (0.1-3 kb) divergently transcribed genes. These regions of DNA are reported to remain hypomethylated in all tissues throughout development (Wise and Pravtcheva (1999) Genomics 60: 258-271). They are often associated with the 5 ends of ubiquitously expressed genes, as well as an estimated 40% of genes showing a tissue-restricted expression profile (Antequera, F. & Bird, A. *Proc. Natl. Acad. Sci. USA* 90, 1195-11999 (1993); Cross, S. H. & Bird, A. P. *Curr. Opin, Genet. Dev.* 5, 309-314 (1995) and are known to be localised regions of active chromatin (Tazi, J. & Bird, A. *Cell* 60, 909-920 (1990).

An 'extended' methylation-free CpG island is a methylation-free CpG island that extends across a region encompassing more than one transcriptional start site and/or extends for more than 300bp and preferably more than 500 bp. The borders of the extended methylation-free CpG island are functionally defined through the use of PCR over the region in combination with restriction endonuclease enzymes whose ability to digest (cut) DNA at their recognition sequence is sensitive to the methylation status of any CpG residues that are present. One such enzyme is HpaII, which recognises and digests at the site CCGG, which is commonly found within CpG islands, but only if the central CG residues are not methylated. Therefore, PCR conducted with HpaII-digested DNA and over a region harbouring HpaII sites, does not give an amplification product due to HpaII digestion if the DNA is unmethylated. The PCR will only give an amplified product if the DNA is methylated. Therefore, beyond the methylation-free region HpaII will not digest the DNA a PCR amplified product will be observed thereby defining the boundaries of the "extended methylation-free CpG island".

International application WO 00/05393 demonstrates that regions spanning methylation-free CpG islands encompassing dual, divergently transcribed promoters from the human TATA binding protein (TBP)/proteosome component-B1 (PSMB1) and heterogeneous nuclear ribonucleoprotein A2/B1 (hnRNPA2)/heterochromatin protein 1Hsγ (HP1$^{Hs\gamma}$) gene loci impart enhanced levels of gene expression to operably linked genes.

Methylation-free CpG islands associated with actively transcribing promoters possess the ability to remodel chromatin and are thus thought to be a prime determinant in establishing and maintaining an open domain at housekeeping gene loci.

UCOEs confer an increased proportion of productive gene integration events with improvements in the level and stability of transgene expression. This has important research and biotechnological applications including the generation of transgenic animals and recombinant protein products in cultured cells.

WO 00/05393 discloses functional UCOE fragments of approximately 4.0 kb, in particular, the '5.5 RNP' fragment defined by nucleotides 4102 to 8286 of FIG. 21 (as disclosed on p 11, lines 6 and 7). The same application discloses a '1.5 kb RNP' fragment (FIGS. 22 and 29, derivation described on p 51, lines 1 to 5). However, this fragment is actually a 2165 bp BamHI-Tth111I fragment of the '5.5 RNP' fragment described above, consisting of nucleotides 4102 to 6267 of FIG. 21 of that application.

A further application, WO 02/24930, discloses artificially-constructed UCOEs composed of fragments of naturally-occurring CpG islands. A third application, WO 04/067701, describes polynucleotides comprising small functional fragments of UCOEs. Such polynucleotides comprise methylation-free CpG islands of no more than approximately 2 kb, or fragments of larger such islands, of not more than approximately 2 kb.

Given the importance of recombinant protein expression in biotechnology, there remains a need for improved expression vectors comprising novel promoter/enhancer combinations.

SUMMARY OF THE INVENTION

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith, As used herein, the term "operably linked" refers to a relationship of operability between elements in the polynucleotides of the invention. "Operably linked" is a term, well known to those of skill in the art, that describes a functional relationship between cis-acting DNA sequences. The exact structural relationship may or may not be relevant and differs for different types of elements. For a promoter, it implies an essentially adjacent (usually within less than 100 bp) position 5' to the open reading frame that it drives. In the case of extended methylation-free CpG islands, it appears that a regional effect on chromatin structure is responsible for increasing the level and consistency of gene expression. By way of example, the element comprising an extended methylation-free CpG-island may be positioned 5' of the enhancer/promoter controlling transcription of the expressible gene. However, "operably-linked" embraces the possibility of its being positioned elsewhere, as long as a clear functional effect can be demonstrated.

By 'functional homologue' is meant a polynucleotide sequence capable of hybridising, under stringent conditions, to the disclosed sequence, and which has similar properties of conferring increased expression of operably-linked expressible open reading frames in two or more tissues. Stringent hybridisation/washing conditions are well known in the art. For example, nucleic acid hybrids that are stable after washing in 0.1×SSC, 0.1% SDS at 60° C. It is well known in the art that optimal hybridisation conditions can be calculated if the sequence of the nucleic acid is known. For example, hybridisation conditions can be determined by the GC content of the nucleic acid subject to hybridisation. See Sambrook et al (1989), Molecular Cloning; A Laboratory Approach. A common formula for calculating the stringency conditions required to achieve hybridisation between nucleic acid molecules of a specified homology is:

$$T_m = 81.5°\ C. + 16.6\ Log\ [Na^{+]+}0.41[\%\ G+C] - 0.63\ (\%\ \text{formamide}).$$

An object of the invention is to provide novel DNA molecules and vectors containing transcriptional enhancers providing very high levels of expression of operably-linked expressible nucleic acid sequences in eukaryotic cells. Advantageously the enhancers may be used in combination with their naturally-associated promoters and/or other genetic elements that increase transcription.

The invention relates to the guinea pig cytomegalovirus early-immediate promoter/enhancer and its use in expression vectors, particularly for obtaining high levels of expression of recombinant proteins. The invention provides eukaryotic expression vectors that are capable of providing increased levels of expression in many cell types over that obtainable from human or murine CMV IE enhancer/promoter elements.

The guinea pig cytomegalovirus early-immediate upstream regulatory region consists of the approximately 1500 bp upstream of the IE1 gene and more especially the sequence disclosed by FIG. 1 and SEQ ID NO: 1. It comprises both promoter and enhancer elements. By 'promoter' is meant at least the transcriptional start site, TATA box and CAAT box, being a fragment comprising nucleotides 779 to 880 of FIG. 1 (SEQ ID NO: 1) or a functional homologue thereof.

Accordingly, the invention provides an isolated polynucleotide comprising at least 100, preferably 200, and more preferably at least 500, contiguous polynucleotides of the guinea pig CMV immediate/early regulatory region as depicted in FIG. 1 and SEQ ID NO:1 and an expressible polynucleotide sequence, transcription of said expressible polynucleotide sequence being driven by a promoter situated between enhancer and gene or other expressible sequence, which may be the endogenous guinea pig CMV immediate/early promoter or some other, heterologous, promoter not naturally associated with the enhancer. The expressible polynucleotide sequence is not a guinea pig CMV immediate/early gene and is not naturally operably linked with the promoter. It will be understood, by one of skill in the art, that in the case of a circular isolated polynucleotide (as in a plasmid vector) by 'between' is meant upstream of the directly operably linked expressible polynucleotide sequence (5' with respect to the sense strand), and downstream (3') of the operably linked enhancer. It is understood that such an isolated polynucleotide may comprise other promoters, not associated with expression of the inserted expressible sequence of interest (such as those required for expression of selectable markers or those associated with other elements).

Hence the isolated polynucleotide comprises
  a) an element comprising at least 200, and preferably at least 500, contiguous nucleotides of SEQ ID NO:1 and
  b) an element comprising an expressible polynucleotide sequence;

characterised in that said isolated polynucleotide comprises, in a 5' to 3' direction with respect to the sense strand of the expressible polynucleotide sequence, an enhancer, a single promoter, and said expressible polynucleotide sequence, and wherein said enhancer is operably linked to said promoter, which is directly operably linked to said expressible polynucleotide sequence and wherein said promoter is not naturally operably linked to said expressible polynucleotide sequence.

Preferably the isolated polynucleotide contains a 5' fragment of the immediate/early regulatory region comprising nucleotides 50 to 550 or, alternatively, a 3' fragment comprising nucleotides 275 to 775. Such fragments contain functional enhancer fragments, without the endogenous promoter.

In one embodiment, therefore, the isolated polynucleotide of the invention comprises at least the promoter from the immediate/early regulatory region of guinea pig CMV directly operably linked to an expressible nucleic acid sequence to which it is not naturally operably linked, said promoter preferably comprising nucleotides 779 to 880 of SEQ ID NO: 1. By 'directly operably linked' is meant that transcription of the gene or other expressible nucleic acid is driven directly from the promoter.

Preferably, said isolated polynucleotide further comprises the enhancer from the major immediate/early regulatory region of guinea pig CMV, more preferably comprising nucleotides 1 to 887 of SEQ ID NO: 1.

In one preferred embodiment, said isolated polynucleotide further comprises an extended, methylation-free CpG island operably linked to said expressible nucleic acid sequence. More preferably, said extended, methylation-free CpG island comprises one or more further promoters, particularly dual or bi-directional promoters that transcribe divergently. Hence the invention provides an isolated polynucleotide comprising at least 200 contiguous nucleotides of FIG. 1 (SEQ ID NO:1), operably linked to an expressible polynucleotide sequence, and further comprising an extended, methylation-free CpG island operably linked to said expressible polynucleotide sequence. Such an extended, methylation-free CpG island may be conveniently situated adjacent to, and upstream of, the enhancer sequence. Preferably such an isolated polynucleotide comprises at least 500 contiguous polynucleotides of FIG. 1 (SEQ ID NO:1), more preferably a 5' fragment of the immediate/early regulatory region comprising nucleotides 50 to 550 or, alternatively, a 3' fragment comprising nucleotides 275 to 775. Most more preferably it comprises nucleotides 1 to 887 of SEQ ID NO: 1.

In one embodiment, said extended, methylation-free CpG island comprises a 44 kb DNA fragment spanning the human TATA binding protein gene and 12 kb each of the 5' and 3' flanking sequence, or functional fragment thereof. Preferably, the functional fragment comprises a 25 kb DNA fragment spanning the human TATA binding protein gene with 1 kb 5' and 5 kb 3' flanking sequence or a functional fragment thereof. More preferably, the functional fragment of the TATA binding protein gene-associated extended, methylation-free CpG island is of not more than 2 kb, further preferably of no more than approximately 1 kb, most preferably comprising a 987 bp BspE1-Esp3I restriction fragment.

In a second embodiment, said extended, methylation-free CpG island comprises a 60 kb DNA fragment spanning the human hnRNP A2 gene with 30 kb 5' and 20 kb 3' flanking sequence, or a functional fragment thereof. Preferably, said functional fragment comprises a 16 kb DNA fragment spanning the human hnRNP A2 gene with 5 kb 5' and 1.5 kb 3' flanking sequence, more preferably a fragment of the human hnRNP A2 gene of no more than 2 kb, more preferably no more than 1.6 kb, comprising a 1546 bp Esp3I restriction fragment. Preferably, said fragment is orientated in forward orientation.

In a third embodiment, the isolated polynucleotide of the present invention comprises a fragment of the β-actin CpG island/promoter region, preferably of human origin, more preferably a DNA fragment within the range of 100 bp to 2 kb spanning the human β-actin CpG island/promoter region.

In a fourth embodiment, the isolated polynucleotide of the present invention comprises a fragment of the PDCD2 CpG island/promoter region, preferably of human origin, more preferably a DNA fragment within the range from 100 bp to 2 kb spanning the human PDCD2 CpG island/promoter region.

In a final alternative embodiment, said extended, CpG-rich unmethylated CpG island is an artificial sequence, not occurring in nature, comprising a DNA fragment within the range from 100 bp to 1.9 kb spanning the human β-actin CpG island/promoter region and a DNA fragment within the range from 100 bp to 2 kb spanning the human PDCD2 CpG island/promoter region. Preferably said fragments are directly adjacent with their promoters oriented divergently.

In a further aspect the invention provides a vector comprising the isolated polynucleotide as described above. The vector may be any vector capable of transferring DNA to a cell. Preferably the vector is a eukaryotic expression vector. Such vectors comprise elements such as promoters and enhancers capable of directing and enhancing transcription in eukaryotic cells. They also preferably contain other features to facilitate and optimise their function. Such features include origins of replication selected to allow replication in the appropriate eukaryotic host cell and also in prokaryotic cells used to manufacture the vectors themselves, one or more selectable markers (often conferring resistance to antibiotics or toxins) allow selection of cells containing the vector in either cell type, elements allowing amplification of the vector or integrated fragments of it, and polylinkers or multicloning sites conveniently situated downstream of the main enhancer/promoter to allow easy insertion of an expressible polynucleotide sequence (commonly referred to as an 'insert') encoding a desired polypeptide product. Such refinements are well-known in the art.

Preferably, the vector is an integrating vector or an episomal vector.

Preferred integrating vectors include recombinant retroviral vectors. A recombinant retroviral vector will include DNA of at least a portion of a retroviral genome which portion is capable of infecting the target cells. The term "infection" is used to mean the process by which a virus transfers genetic material to its host or target cell. Preferably, the retrovirus used in the construction of a vector of the invention is also rendered replication-defective to remove the effect of viral replication of the target cells. In such cases, the replication-defective viral genome can be packaged by a helper virus in accordance with conventional techniques. Generally, any retrovirus meeting the above criteria of infectiousness and capability of functional gene transfer can be employed in the practice of the invention.

Suitable retroviral vectors include but are not limited to pLJ, pZip, pWe and pEM, well known to those of skill in the art. Suitable packaging virus lines for replication-defective retroviruses include, for example, ΨCrip, ΨCre, Ψ2 and ΨAm.

Other vectors useful in the present invention include adenovirus, adeno-associated virus, SV40 virus, vaccinia virus, HSV and poxvirus vectors. A preferred vector is the adenovirus. Adenovirus vectors are well known to those skilled in the art and have been used to deliver genes to numerous cell types, including airway epithelium, skeletal muscle, liver, brain and skin (Hitt et al, 1997; Anderson, 1998).

A further preferred vector is the adeno-associated (AAV) vector. AAV vectors are well known to those skilled in the art and have been used to stably transduce human T-lymphocytes, fibroblasts, nasal polyp, skeletal muscle, brain, erythroid and haematopoietic stem cells for gene therapy applications. International Patent Application WO 91/18088 describes specific AAV based vectors.

Preferred episomal vectors include transient non-replicating episomal vectors and self-replicating episomal vectors with functions derived from viral origins of replication such as those from EBV, human papovavirus (BK) and BPV-1. Such integrating and episomal vectors are well known to those skilled in the art and are fully described in the body of literature well known to those skilled in the art. In particular, suitable episomal vectors are described in WO98/07876.

Mammalian artificial chromosomes can also be used as vectors in the present invention. The use of mammalian artificial chromosomes is discussed by Calos (1996).

In a preferred embodiment, the vector of the present invention is a plasmid. The plasmid may be a non-replicating, non-integrating plasmid.

The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures.

A non-replicating, non-integrating plasmid is a nucleic acid which when transfected into a host cell does not replicate and does not specifically integrate into the host cell's genome (i.e. does not integrate at high frequencies and does not integrate at specific sites).

Highly preferred embodiments of vectors of the invention comprise nucleotides 1 to 1003 and 1747 to 5749 of SEQ ID NO: 2; nucleotides 1 to 9328 and 10072 to 14119 of SEQ ID NO: 3; or nucleotides 1 to 2592 and 3336 to 7383 of SEQ ID NO: 4, being expression vectors suitable for insertion of an expressible sequence in place of the exemplary enhanced green fluorescent protein reporter encoded by the full sequences.

The present invention also provides a host cell transfected with the vector of the present invention. The host cell may be any eukaryotic cell. Preferably it is a mammalian cell, more preferably a human or rodent cell.

Numerous techniques are known and are useful according to the invention for delivering the vectors described herein to cells, including the use of nucleic acid condensing agents, electroporation, complexing with asbestos, polybrene, DEAE cellulose, Dextran, liposomes, cationic liposomes, lipopolyamines, polyornithine, particle bombardment and direct microinjection.

A vector of the invention may be delivered to a host cell non-specifically or specifically (i.e. to a designated subset of host cells) via a viral or non-viral means of delivery. Preferred delivery methods of viral origin include viral particle-producing packaging cell lines as transfection recipients for the vector of the present invention into which viral packaging signals have been engineered, such as those of adenovirus, herpes viruses and papovaviruses. Preferred non-viral based gene delivery means and methods may also be used in the invention and include direct naked nucleic acid injection, nucleic acid condensing peptides and non-peptides, cationic liposomes and encapsulation in liposomes.

Delivery of a vector according to the invention is contemplated using nucleic acid condensing peptides. Nucleic acid condensing peptides, which are particularly useful for condensing the vector and delivering the vector to a cell, are described in International Patent Application WO 96/41606. Functional groups may be bound to peptides useful for delivery of a vector according to the invention, as described in WO 96/41606. These functional groups may include a ligand that targets a specific cell-type such as a monoclonal antibody, insulin, transferrin, asialoglycoprotein, or a sugar. The ligand thus may target cells in a non-specific manner or in a specific manner that is restricted with respect to cell type.

The functional groups also may comprise a lipid, such as palmitoyl, oleyl, or stearoyl; a neutral hydrophilic polymer such as polyethylene glycol (PEG), or polyvinylpyrrolidine (PVP); a fusogenic peptide such as the HA peptide of influenza virus; or a recombinase or an integrase. The functional group also may comprise an intracellular trafficking protein such as a nuclear localisation sequence (NLS), an endosome escape signal such as a membrane disruptive peptide, or a signal directing a protein directly to the cytoplasm.

The invention further provides a host cell comprising an isolated polynucleotide or vector as herein described. Preferably said cell is a eukaryotic cell, more preferably a mammalian cell, further preferably a human or rodent cell.

In a further aspect, the invention provides a method of expressing an expressible polynucleotide, preferably encoding a polypeptide, comprising inserting an isolated polynucleotide according to the invention into a suitable expression vector as described herein and further inserting said vector into a suitable host cell as described herein and culturing said host cell in suitable conditions to allow expression.

Preferably, said polypeptide is a therapeutically useful polypeptide, preferably selected from the list consisting of an immunoglobulin or a functional epitope-binding fragment of an immunoglobulin, a growth factor, a receptor or soluble fragment thereof and a blood clotting factor.

Also provided is a pharmaceutical preparation comprising a polynucleotide, vector or host cell according to the invention and a pharmaceutically acceptable carrier, excipient, buffer or medium.

BRIEF DESCRIPTION OF THE DRAWINGS

The present invention will now be described, by way of example only, with reference to the accompanying drawings, in which:

FIG. 1 shows the nucleotide sequence of the GPCMV IE enhancer/promoter (SEQ ID NO: 1). Potential binding sites for the transcription factors AP-1 NF-kB, SRF and GCN4 are shown, together with CAAT and TATA boxes, the CRS initiator site and transcriptional start (arrow).

DETAILED DESCRIPTION

Figure 2:
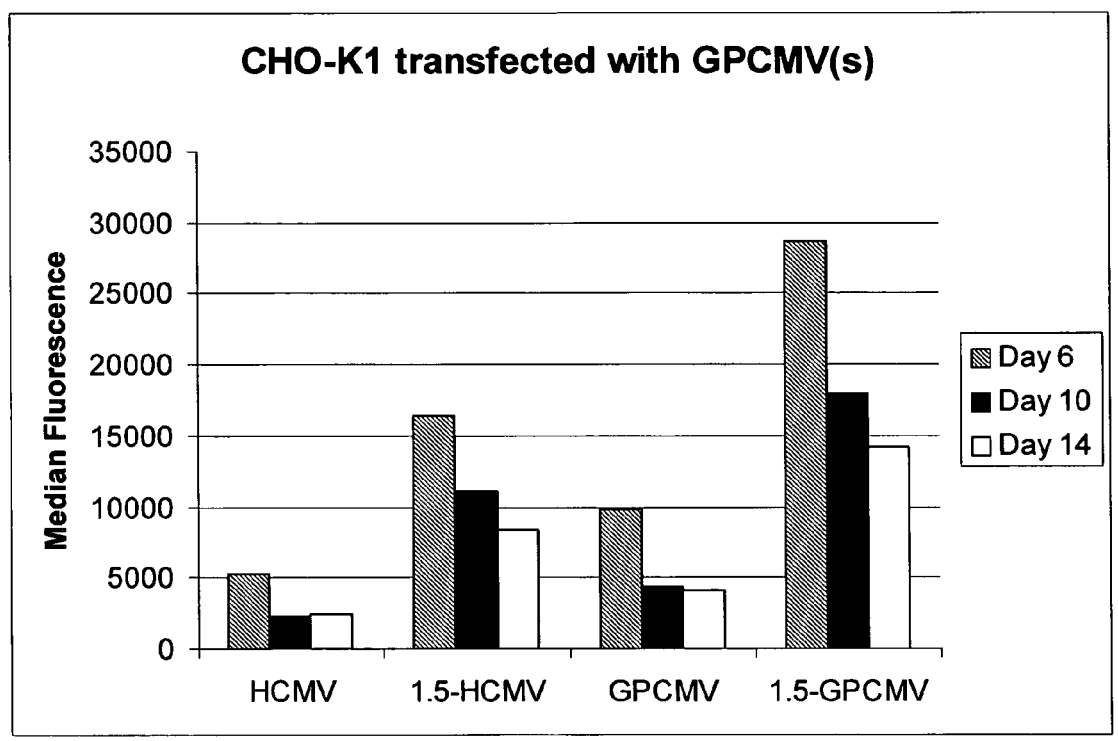
FIG. 2 shows expression levels obtained with a number of EGFP reporter constructs in CHO-K1 cells, expressed as median fluorescence as measured by FACS. The results compare human and guinea pig CMV IE enhancer/promoters, with and without a 1.5 kb hnRNP UCOE element.

The following examples of some embodiments of the invention are provided without limiting the invention to only those embodiments described herein.

EXAMPLE 1

Generation of Stably Transfected CHO-K1 Cells Using Vectors Containing Either the hCMV Promoter or the gpCMV Promoter The plasmids constructs were generated as follows. The ampicillin resistance gene was isolated from pBluescript® (Stratagene) by PCR incorporating NruI sites within each end of the primer (5'-TGTCGCGAGTCTGACAGTTACCAAT GCTTAATC 3' (SEQ ID NO:5),
5'-CATCGCGAGCACTTTTCGGGGAAATGT-GTGCGC-3' (SEQ ID NO: 6). The PCR product was inserted into the PvuII site of pMaeII (Nucleic Acids Research 2001 29:E26) to generate pCA1. The following oligonucleotides

```
1.  5'- TCGAAGTTTAAACATTTAAATCTAGAAG  (SEQ ID NO:7)
    CTTAT-3'

2.  5'-CCGGTATCGATAAGCTTCTAGATTTAAAT  (SEQ ID NO:8)
    GTTTAAACT-3'

3.  5'-CGATACCGGTGGCGCGCCAATTGTTAATT  (SEQ ID NO:9)
    AAGATCTGG-3'

4.  5'-CCCATTGGGCCAGATCTTAATTAACAATT  (SEQ ID NO:10)
    GGCGCGCCA-3'

5.  5'-CCCAATGGGCCGTACGAATTCCTTAGGCT  (SEQ ID NO:11)
    CGAG-3'

6.  5'-GGCCCTCGAGCCTAAGGAATTCGTACGG-  (SEQ ID NO:12)
    3'
``` were annealed (1 with 2; 3 with 4; 5 with 6; and then the three dimers were annealed together) and used to replace the multicloning site of pCA1 between the XhoI and NotI sites destroying these sites during the construction. This generated pCA1MCS. The AgeI site was deleted from the PGK promoter within pPGK-Puro-bgh pA by AgeI restriction digestion followed by blunting with T4 DNA polymerise and re-ligation. The PGK-Puromycin pA cassette was removed from this vector as an EcoRI-XhoI fragment and ligated into pCA1MCS that had similarly been digested with EcoRI and XhoI. This vector was designated pCIA-Puro (CET 1000). The bghpA in pCIA-Puro was then replaced with the HSV TkpA. The HSV-Tk polyA was removed from pEGFP-N1 as a BstBI-Eco1091 fragment, blunted with T4 DNA polymerase, and ligated into pCIA-Puro that had been digested with SacI and blunted with T4 DNA polymerase. This vector was designated CET 1005.

To construct pCET1005 1.5 kb-GPCMV-EGFP, the 1.5 kb hnRNP UCOE fragment was excised from pCET20 (described previously) using BsmBI, blunt-ended using T4 polymerase and then cloned into the blunted XhoI site of pEGFP-N1 (Clontech, Palo Alto, Calif., USA) generating pEGFP-N1 1.5 kb-EGFP. The 2.4 kb "hnRNP-EGFP" cassette was then excised from this plasmid using NheI (blunt-ended)/NotI and subcloned into the backbone of pCET1005-EGFP that had been digested with SwaI/NotI to give pCET1005 1.5 kb-EGFP. The GPCMV promoter was then excised from pPCR-Script GPCMV (synthesized by Geneart, Regensburg, Germany) with NheI and EcoRI, blunt-ended and subcloned into the blunted BamHI of this plasmid to yield pCET1005 1.5 kb-GPCMV-EGFP. Excising the 1.5 kb hnRNP UCOE using PmeI/SacI, blunt-ending and religating the backbone generated the plasmid pCET1005 GPCMV-EGFP.

To construct pCET1015 8 kb-GPCMV-EGFP, the 5.3 kb SacI (blunt)/PacI fragment of pCET1005 1.5 kb-GPCMV-EGFP was subcloned into the AscI (blunt)/PacI-digested backbone of pCET1015. The plasmid pCET1005 1.5 kb-HCMV-EGFP was constructed by subcloning the blunted 1.5 kb hnRNP BsmBI fragment from pCET20 into the blunted ClaI site of pCET1005-EGFP.

Figure 3:
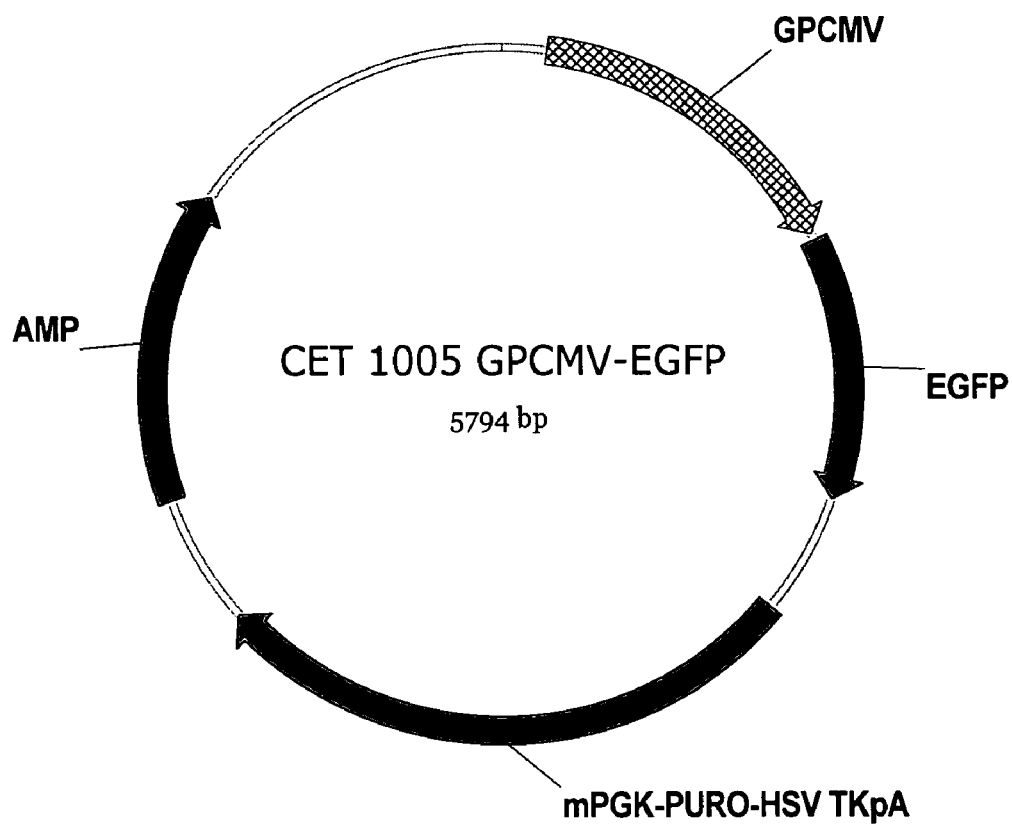
FIG. 3 shows a map of reporter plasmid CET 1005 GPCMV-EGFP comprising the GPCMV IE enhancer/promoter (GPCMV) driving expression of an enhanced green fluorescence protein reporter gene (EGFP). The eukaryotic selectable marker is a puromycin resistance gene expressed from a mouse phosphoglycerate kinase promoter. The prokaryotic selectable marker is ampicillin resistance.
Figure 4:
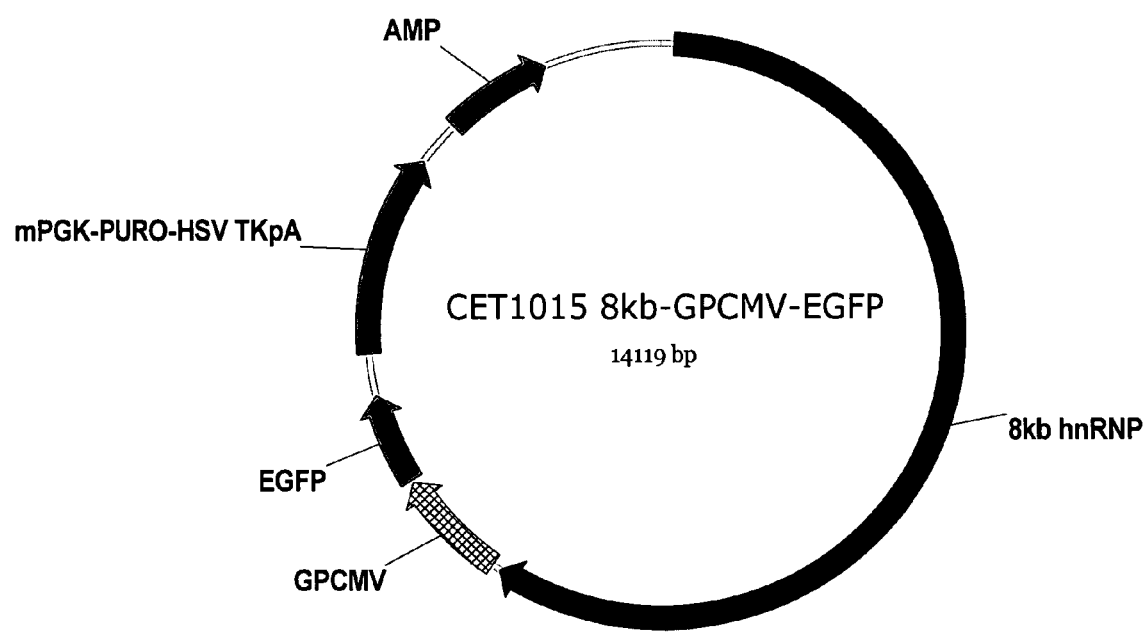
FIG. 4 shows a map of reporter plasmid CET1015 8 kb-GPCMV-EGFP. This is similar to CET 1005 GPCMV-EGFP with the addition of the 8 kb hnRNP UCOE element upstream of the GPCMV IE enhancer/promoter.
Figure 5:
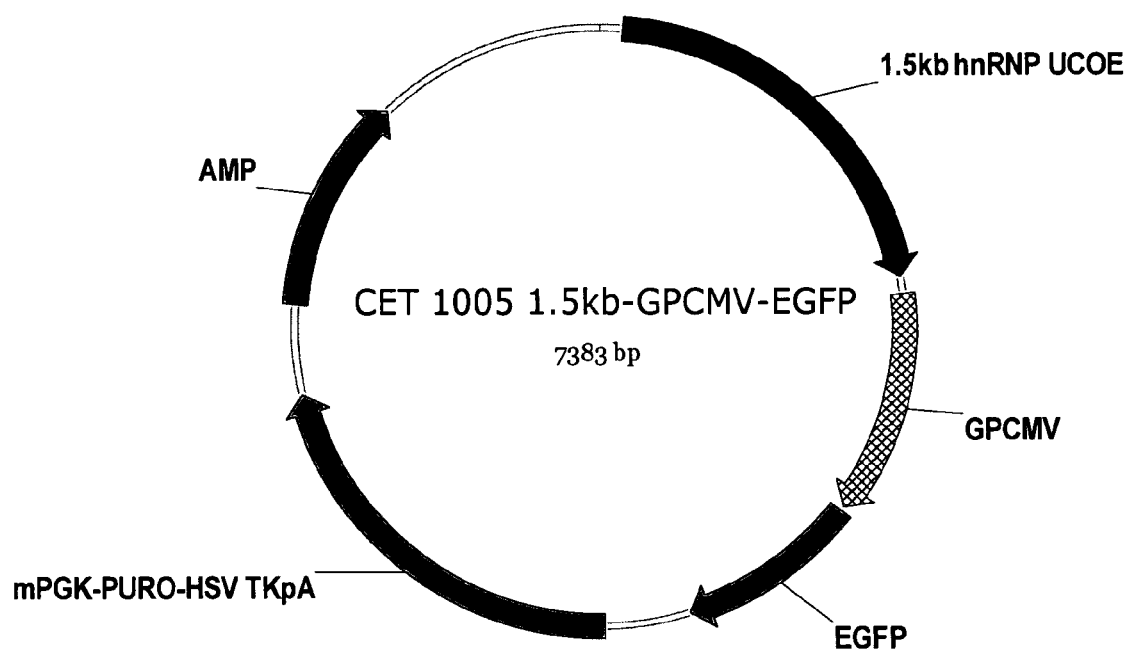
FIG. 5 shows a map of reporter plasmid CET101 1.5 kb-GPCMV-EGFP. This is similar to CET 1015 8 kb-GPCMV-EGFP with the replacement of the 8 kb hnRNP UCOE with a 1.5 kb hnRNP UCOE element.

CHO-K1 cells were maintained in F12 (HAM) nutrient mixture (Gibco, UK) supplemented with 10% Foetal Calf Serum (Invitrogen, UK) and 5 U/ml Penicillin and Streptomycin mix (Sigma, UK). For stable transfection of CHO-K1, plasmids were linearised with PciI, extracted in phenol: chloroform: isoamyl alcohol and chloroform, precipitated in ethanol and resuspended at a concentration of 0.25 µg/µl in sterile water. In a sterile electroporation cuvette, equivalent molar quantities of linearised plasmids were diluted to 25 µl in sterile water (1.39 µg pCET1005-EGFP, 1.78 µg pCET1005 1.5 kb-HCMV-EGFP, 1.45 µg pCET1005 GPCMV-EGFP or 1.85 µg pCET1005 1.5 kb-GPCMV-EGFP) and mixed with $5 \times 10^6$ CHO-K1 cells in 250 µl growth medium. After incubation on ice for 15 minutes, the cells were electroporated at 250V/975 µF (BioRad Gene Pulser II™) and incubated at room temperature for a further 10 minutes. Cells were then transferred into 10 ml of growth media, harvested by centrifugation and transferred into a 225 cm² tissue culture flask in a total of 50ml of growth medium. Cells were incubated for 24 hours at 37° C. in a 5% $CO_2$ incubator before addition of Puromycin (Sigma, UK) to a concentration of 12.5 µg/ml. Cells were cultured for 8 days (replacing selective media after 4 days) before the stable transfectants were harvested, subcultured in 6-well tissue culture dishes (maintaining selection) and analysed by Fluorescence Activated Cell Sorting using the FL1 channel to view EGFP. FIG. 2 clearly shows that the two gpCMV containing constructs pCET1005-GPCMV-EGFP (FIG. 3) and pCET1005-1.5 kb-GPCMV-EGFP (FIG. 5) generate pools which express the transgene to a higher level than the corresponding constructs which use the hCMV promoter, pCET1005-EGFP and pCET1005-1.5 kb-HCMV-EGFP respectively.

EXAMPLE 2

Figure 6:
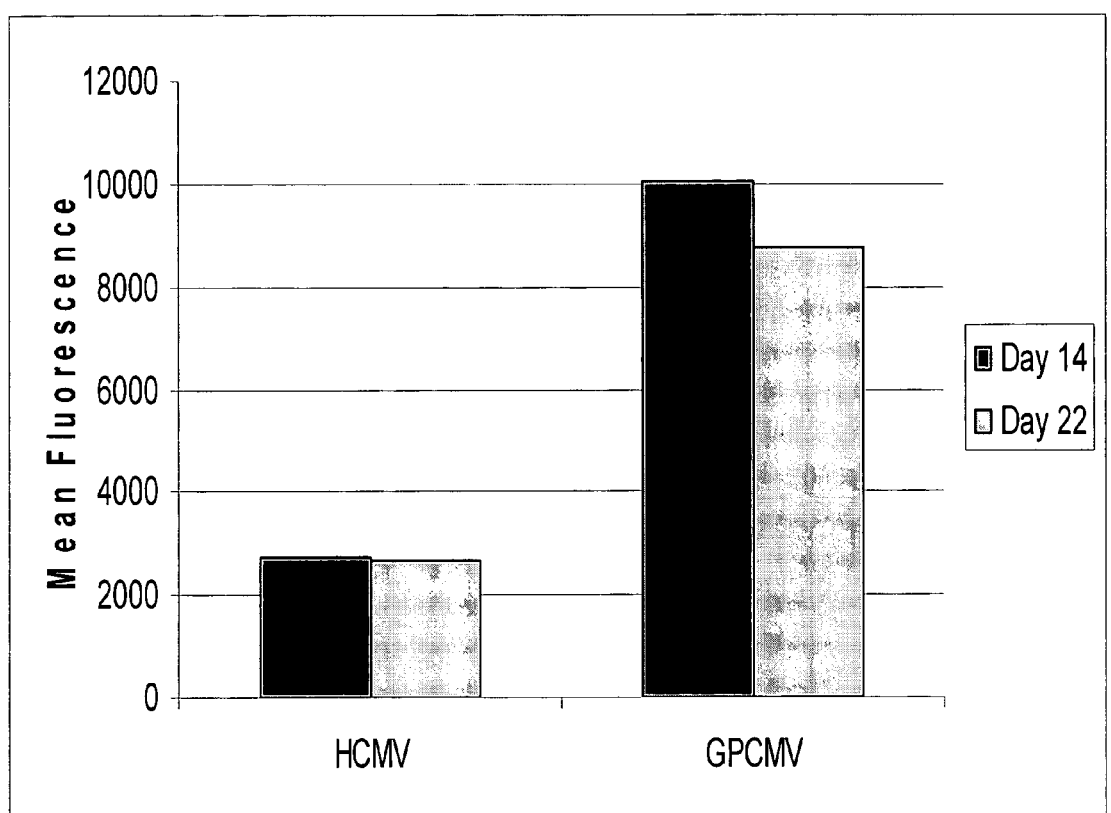
FIG. 6 compares EGFP expression driven by human and guinea pig CMV IE enhancer/promoter elements in HEK293 cells (human embryonic kidney cells transformed with sheared adenovirus type 5 DNA)

HEK293 cells were maintained in Dulbecco's Modified Eagle Medium (DMEM; Sigma, UK) supplemented with 10% Foetal Calf Serum and 5 U/ml Penicillin and Streptomycin mix. For stable transfection, HEK293 cells were seeded into 6-well dishes at a density of $1 \times 10^6$ cells/well and cultured for 24 hours at 37° C. in a 5% $CO_2$ incubator. Cells were then transfected with 4 µg of the indicated plasmid (pCET1005-EGFP or pCET1005-gpCMV-EGFP)(linearised with PciI) using 10 µl Lipofectamine 2000 (Invitrogen, UK). The DNA and Lipofectamine 2000 were diluted separately in 250 µl OptiMEM I (Gibco, UK) and, after incubation at room temperature for 5 minutes, mixed together and incubated for a further 20 minutes. Growth media on the cells was replaced with 1 ml of OptiMEM I supplemented with 15% FCS and the DNA/Lipofectamine 2000 mixture was then added. Cells were incubated at 37° C. in a 5% $CO_2$ incubator for 5 hours before 3.5 ml of OptiMEM I supplemented with 10% FCS was added. Cells were then incubated at 37° C. in a 5% $CO_2$ incubator for 24 hours before being harvested and transferred to a 225 cm$^2$ tissue culture flask in a total of 50 ml of DMEM growth medium, supplemented with 0.5 μg/ml Puromycin. Cells were grown for approximately 14 days (replacing the selective media every 3-4 days) before the stable transfectants were harvested by centrifugation, subcultured in 6-well tissue culture dishes (maintaining selection) and analysed by Fluorescence Activated Cell Sorting using the FL1 channel to view EGFP. FIG. 6 shows that the pools generated with the gpCMV construct give EGFP expression levels three to four fold higher than those generated with the hCMV construct.

EXAMPLE 3

Figure 7:
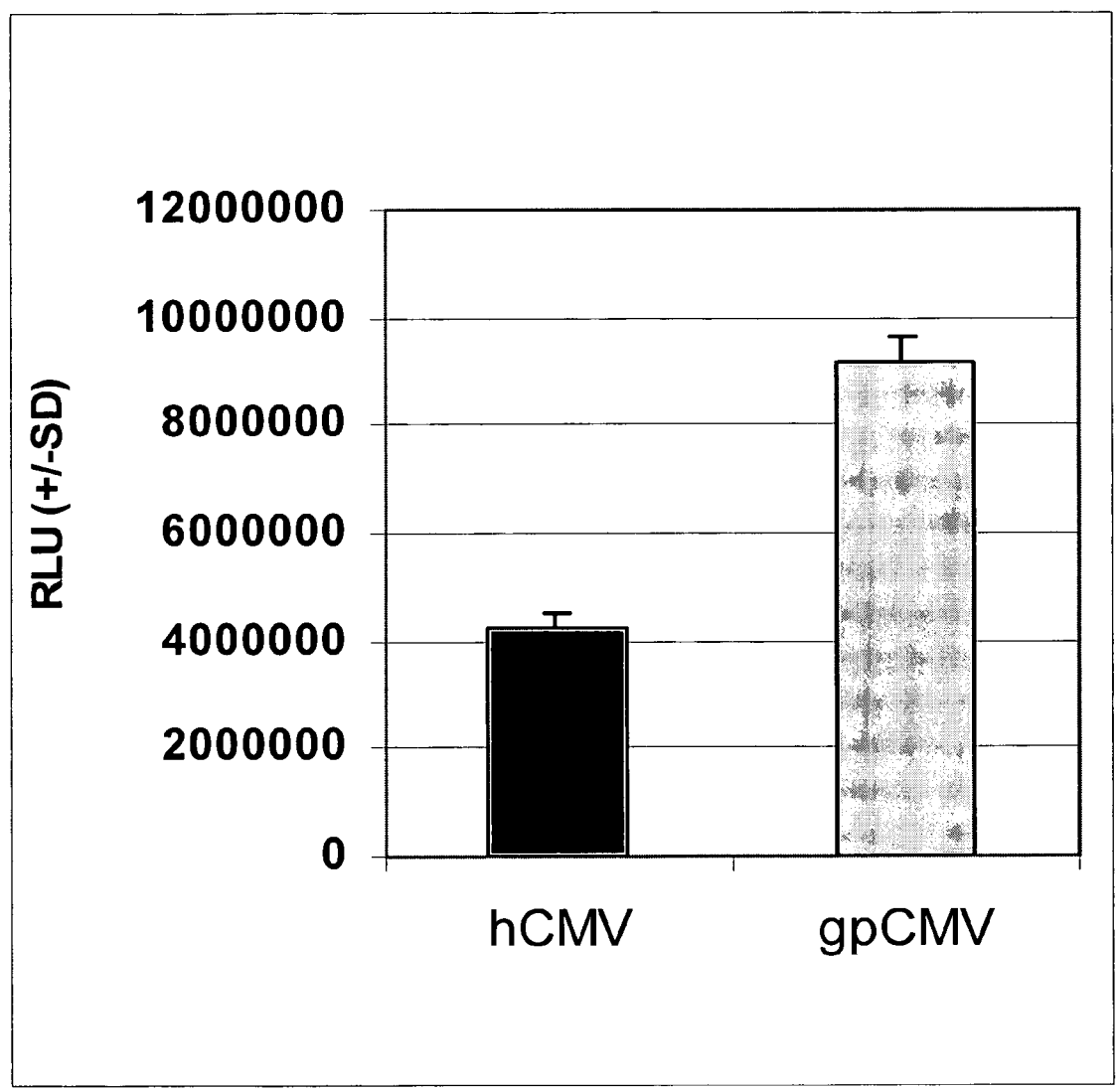
FIG. 7 shows a similar comparison using luciferase-based reporter constructs.

CHO-K1 cells were cultured as described for Example 1. 1.5×10$^5$ CHO-K1 cells were seeded 24 hrs before transfection into 12-wells. 24 hrs later, cells were transfected with 1 ug Luciferase reporter plasmid (phCMV-Luc or pgpCMV-Luc) using 1.5 ul FUGENE (Roche, UK). For this, FUGENE and DNA were both diluted separately in Opti-MEM I (Invitrogen), mixed together and incubated for 30 min at RT before added to the cells. Luciferase expression was analysed 24 hrs later using a Berthold luminometer (Berthold, Wildbad, Germany). Generally, cell lysis and luciferase reporter assay were performed as described earlier (Lipinski et al., Gene Therapy, 2001 (8): 274-281). Transfections were done in triplicate and the mean and standard deviation of one representative experiment are shown (FIG. 7). Clearly the gpCMV vector was at least two-fold more active luciferase than the hCMV plasmid.

The plasmid hCMV-Luc has been described earlier (Lipinski et al., Gene Therapy (2001) 8: 274-281). The plasmid gpCMV-Luc was generated by preparing a NdeI/EcoRI fragment from pCRScript/gpCMV (customer gene synthesis company: Geneart, Regensburg, Germany) and cloning this gpCMV promoter fragment into the blunted XhoI site of pGL3basic (Promega).

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements. It is intended that the following claims define the scope of the invention and that the systems, methods, and compositions within the scope of these claims and their equivalents be covered thereby.

What is claimed is:

1. An isolated polynucleotide comprising:
   (a) an element comprising at least 200 contiguous nucleotides of SEQ ID NO:1; and
   (b) an element comprising an expressible polynucleotide sequence, wherein said element in (a) is directly operably linked to said expressible polynucleotide sequence in (b) and is not naturally operably linked to said expressible polynucleotide sequence.

2. An isolated polynucleotide according to claim 1, comprising at least 500 contiguous nucleotides of SEQ ID NO: 1.

3. An isolated polynucleotide according to either of claim 1 or 2, comprising nucleotides 50 to 550 of SEQ ID NO: 1.

4. An isolated polynucleotide according to either of claim 1 or 2, comprising nucleotides 275 to 775 of SEQ ID NO: 1.

5. An isolated polynucleotide according to either of claim 1 or 2, wherein the element in (a) comprises the promoter from the immediate/early regulatory region of guinea pig CMV.

6. An isolated polynucleotide according to claim 5, comprising nucleotides 679 to 880 of SEQ ID NO: 1.

7. An isolated polynucleotide according to claim 1 or claim 2, comprising nucleotides 1 to 887 of SEQ ID NO:1

8. An isolated polynucleotide according to claim 1 or claim 2, further comprising an extended, methylation-free CpG island operably linked to said expressible nucleic acid sequence.

9. A vector comprising the polynucleotide of claim 1 or claim 2.

10. A eukaryotic expression vector according to claim 9.

11. A vector according to claim 9, comprising the polynucleotide sequence of nucleotides 1 to 1003 and 1747 to 5749 of SEQ ID NO: 2.

12. A vector according to claim 9, comprising nucleotides 1 to 9328 and 10072 to 14119 of SEQ ID NO: 3.

13. A vector according to claim 9, comprising nucleotides 1 to 2592 and 3336 to 7383 of SEQ ID NO: 4.

14. An isolated host cell comprising an isolated polynucleotide according to any of claims 1 or 2, or a vector comprising the polynucleotide of claim 1.

15. A method of expressing a polypeptide comprising inserting an expressible nucleic acid sequence encoding said polypeptide into an expression vector according to claim 9 into an appropriate host cell and culturing said host cell in suitable conditions to allow expression.

16. The method according to claim 15, wherein said polypeptide is a therapeutically useful polypeptide.

17. The method according to claim 16, wherein said polypeptide is selected from the group consisting of: an immunoglobulin, a functional epitope-binding fragment of an immunoglobulin, a growth factor, a soluble receptor and a blood clotting factor.

18. A pharmaceutical preparation comprising a polynucleotide according to claim 1 or claim 2, a vector comprising the polynucleotide of claim 1, or a host cell according to claim 1 and a pharmaceutically acceptable carrier, excipient, buffer or medium.

* * * * *

SEQUENCE LISTING

<160> NUMBER OF SEQ ID NOS: 12

<210> SEQ ID NO 1
<211> LENGTH: 887
<212> TYPE: DNA
<213> ORGANISM: Guinea pig cytomegalovirus

<400> SEQUENCE: 1

```
ttagtcatat gttacttggc agaggccgca tggaaagtcc ctggacgtgg gacatctgat      60
taatacgtga ggaggtcagc catgttcttt ttggcaaagg actacggtca ttggacgttt     120
gattggcatg ggatagggtc agccagagtt aacagtgttc ttttggcaaa gggatacgtg     180
gaaagtcccg ggccatttac agtaaactga tacggggaca aagcacagcc atatttagtc     240
atgtattgct tggcagaggg tctatggaaa gtccctggac gtgggacgtc tgattaatat     300
gaaagaaggt cagccagagg tagctgtgtc cttttttggca aagggatacg gttatgggac     360
gtttgattgg actgggatag ggtcagccag agttaacagt gttctttttgg caaaggaaac     420 gtggaaagtc ccgggccatt tacagtaaac tgatactggg acaaagtaca cccatattta     480
gtcatgttct ttttggcaaa gagcatctgg aaagtcccgg gcagcattat agtcacttgg     540
cagagggaaa gggtcactca gagttaagta catctttcca gggccaatat tccagtaaat     600
tacacttagt tttatgcaaa tcagccacaa aggggatttt cccggtcaat tatgactttt     660
tccttagtca tgcggtatcc aattactgcc aaattggcag tacatactag gtgattcact     720
gacatttggc cgtcctctgg aaagtccctg gaaaccgctc aagtactgta tcatggtgac     780 tttgcattt tggagagcac gccccactcc accattggtc cacgtacccct atgggggagt     840
```

```
ggtttatgag tatataaggg gctccggttt agaagccggg cagagcg        887

<210> SEQ ID NO 2
<211> LENGTH: 5794
<212> TYPE: DNA
<213> ORGANISM: Artificial
<220> FEATURE:
<223> OTHER INFORMATION: Eukaryotic expression vector

<400> SEQUENCE: 2
cgttgtaaaa cgacggccag tgaattgtaa tacgactcac tatagggcga attgggtacc      60
gggccccccc tcgaagtttc aagcttcgaa ttctgcagtc gacggtaccg cgggcccggg     120
atctatgtta cttggcagag gccgcatgga aagtccctgg acgtgggaca tctgattaat     180
acgtgaggag gtcagccatg ttcttttttgg caaaggacta cggtcattgg acgtttgatt     240
ggcatgggat agggtcagcc agagttaaca gtgttctttt ggcaaaggga tacgtggaaa     300
gtcccgggcc atttacagta aactgatacg gggacaaagc acagccatat ttagtcatgt     360
attgcttggc agagggtcta tggaaagtcc ctggacgtgg gacgtctgat taatatgaaa     420
gaaggtcagc cagaggtagc tgtgtccttt ttggcaaagg gatacggtta tgggacgttt     480
gattggactg ggatagggtc agccagagtt aacagtgttc ttttggcaaa ggaaacgtgg     540
aaagtcccgg gccatttaca gtaaactgat actgggacaa agtacaccca tatttagtca     600 tgttctttt ggcaaagagc atctggaaag tcccgggcag cattatagtc acttggcaga     660
gggaaagggt cactcagagt taagtacatc tttccagggc caatattcca gtaaattaca     720
cttagtttta tgcaaatcag ccacaaaggg gatttttccg gtcaattatg acttttttcct     780 tagtcatgcg gtatccaatt actgccaaat tggcagtaca tactaggtga ttcactgaca     840
tttggccgtc ctctggaaag tccctggaaa ccgctcaagt actgtatcat ggtgactttg     900
catttttgga gagcacgccc cactccacca ttggtccacg tacccatatgg gggagtggtt     960 tatgagtata aaggggctc cggtttagaa gccgggcaga gcggaattga tccaccggtc    1020
gccaccatgg tgagcaaggg cgaggagctg ttcaccgggg tggtgcccat cctggtcgag    1080
ctggacggcg acgtaaacgg ccacaagttc agcgtgtccg gcgagggcga gggcgatgcc    1140
acctacggca agctgaccct gaagttcatc tgcaccaccg gcaagctgcc cgtgccctgg    1200
cccaccctcg tgaccaccct gacctacggc gtgcagtgct tcagccgcta ccccgaccac    1260
atgaagcagc acgacttctt caagtccgcc atgcccgaag gctacgtcca ggagcgcacc    1320
atcttcttca aggacgacgg caactacaag acccgcgccg aggtgaagtt cgagggcgac    1380
accctggtga accgcatcga gctgaagggc atcgacttca aggaggacgg caacatcctg    1440
gggcacaagc tggagtacaa ctacaacagc cacaacgtct atatcatggc cgacaagcag    1500
aagaacggca tcaaggtgaa cttcaagatc cgccacaaca tcgaggacgg cagcgtgcag    1560
ctcgccgacc actaccagca gaacaccccc atcggcgacg gccccgtgct gctgcccgac    1620
aaccactacc tgagcaccca gtccgccctg agcaaagacc ccaacgagaa gcgcgatcac    1680
atggtcctgc tggagttcgt gaccgccgcc gggatcactc tcggcatgga cgagctgtac    1740
aagtaaagcg gccgcgactc tagatcataa tcagccatac cacatttgta gaggttttac    1800
ttgctttaaa aaacctccca cacctccccc tgaacctgaa acataaaatg aatgcaattg    1860
ttgttgttaa cttgtttatt gcagcttata atggttacaa ataaagcaat agcatcacaa    1920
atttcacaaa taaagcattt ttttcactgc attctagttg tggtttgtcc aaactcatca    1980
```

```
atgtatctta actagagtcg acctgcaggc atgcaagctt accggtggcg cgcgcgccaa    2040
ttgttaatta agatctggcc caatgggccg tacgaattcc ttaggctacc gggtagggga    2100
ggcgcttttc ccaaggcagt ctggagcatg cgctttagca gccccgctgg gcacttggcg    2160
ctacacaagt ggcctctggc ctcgcacaca ttccacatcc accggccggt aggcgccaac    2220
cggctccgtt ctttggtggc cccttcgcgc caccttctac tcctcccta  gtcaggaagt    2280
tccccccgc  cccgcagctc cgtcgtgca  ggacgtgaca aatggaagta gcacgtctca    2340
ctagtctcgt gcagatggac agcaccgctg agcaatggaa gcgggtaggc ctttggggca    2400
gcggccaata gcagctttgc tccttcgctt tctgggctca gaggctggga aggggtgggt    2460
ccggggcgg  gctcagggc  gggctcaggg gcgggcggg  cgcccgaagg tcctccggag    2520
gcccggcatt ctgcacgctt caaaagcgca cgtctgccgc gctgttctcc tcttcctcat    2580
ctccgggcct ttcgaccagc ttaccatgac cgagtacaag cccacggtgc gcctcgccac    2640
ccgcgacgac gtcccagggg ccgtacgcac cctcgccgcc gcgttcgccg actacccgc    2700
cacgcgccac accgtcgatc cggaccgcca catcgagcgg gtcaccgagc tgcaagaact    2760
cttcctcacg cgcgtcgggc tcgacatcgg caaggtgtgg gtcgcggacg acggcgccgc    2820
ggtggcggtc tggaccacgc cggagagcgt cgaagcgggg gcggtgttcg ccgagatcgg    2880
cccgcgcatg gccgagttga gcggttcccg gctggccgcg cagcaacaga tggaaggcct    2940
cctggcgccg caccggccca aggagcccgc gtggttcctg gccaccgtcg gcgtctcgcc    3000
cgaccaccag ggcaagggtc tgggcagcgc cgtcgtgctc cccggagtgg aggcggccga    3060
gcgcgccggg gtgcccgcct tcctggagac ctccgcgccc cgcaacctcc ccttctacga    3120
gcggctcggc ttcaccgtca ccgccgacgt cgaggtgccc gaaggaccgc gcacctggtg    3180
catgacccgc aagcccggtg cctgacgccc gccccacgac ccgcagcgcc cgaccgaaag    3240
gagcgcacga ccccatgcat cgtagacgaa atgaccgacc aagcgacgcc caacctgcca    3300
tcacgagatt tcgattccac cgccgccttc tatgaaaggt tgggcttcgg aatcgttttc    3360
cgggacgccg gctggatgat cctccagcgc ggggatctca tgctggagtt cttcgcccac    3420
cctaggggga ggctaactga aacacggaag gagacaatac cggaaggaac ccgcgctatg    3480
acggcaataa aaagacagaa taaaacgcac ggtgttgggt cgtttgttca taaacgcggg    3540
gttcggtccc agggctggca ctctgtcgat accccaccga gaccccattg gggccaatac    3600
gcccgcgttt cttcctttc  cccaccccac ccccaagtt  cgggtgaagg cccagggctc    3660
gcagccaacg tcgggcggc  aggcccccag cttttgttcc ctttagtgag ggttaatttc    3720
gagcttggcg taatcatggt catagctgtt cctgtgtga  aattgttatc cgctcacaat    3780
tccacacaac atacgagccg gaagcataaa gtgtaaagcc tggggtgcct aatgagtgag    3840
ctaactcaca ttaattgcgt tgcgctcact gcccgctttc cagtcgggaa acctgtcgtg    3900
ccagcatcgc gagcactttt cggggaaatg tgcgcggaac ccctatttgt ttatttttct    3960
aaatacattc aaatatgtat ccgctcatga caataaacc  ctgataaatg cttcaataat    4020
attgaaaaag gaagagtatg agtattcaac atttccgtgt cgcccttatt cccttttttg    4080
cggcattttg ccttcctgtt tttgctcacc cagaaacgct ggtgaaagta aaagatgctg    4140
aagatcagtt gggtgcacga gtgggttaca tcgaactgga tctcaacagc ggtaagatcc    4200
ttgagagttt tcgccccgaa gaacgttttc caatgatgag cacttttaaa gttctgctat    4260
gtggcgcggt attatcccgt attgacgccg ggcaagagca actcggtcgc cgcatacact    4320
attctcagaa tgacttggtt gagtactcac cagtcacaga aaagcatctt acggatggca    4380
```

```
tgacagtaag agaattatgc agtgctgcca taaccatgag tgataacact gcggccaact    4440
tacttctgac aacgatcgga ggaccgaagg agctaaccgc ttttttgcac aacatggggg    4500
atcatgtaac tcgccttgat cgttgggaac cggagctgaa tgaagccata ccaaacgacg    4560
agcgtgacac cacgatgcct gtagcaatgg caacaacgtt gcgcaaacta ttaactggcg    4620
aactacttac tctagcttcc cggcaacaat taatagactg gatggaggcg gataaagttg    4680
caggaccact tctgcgctcg gcccttccgg ctggctggtt tattgctgat aaatctggag    4740
ccggtgagcg tgggtctcgc ggtatcattg cagcactggg gccagatggt aagccctccc    4800
gtatcgtagt tatctacacg acggggagtc aggcaactat ggatgaacga aatagacaga    4860
tcgctgagat aggtgcctca ctgattaagc attggtaact gtcagactcg cgacactgca    4920
ttaatgaatc ggccaacgcg cggggagagg cggtttgcgt attgggcgct cttccgcttc    4980
ctcgctcact gactcgctgc gctcggtcgt tcggctgcgg cgagcggtat cagctcactc    5040
aaaggcggta atacggttat ccacagaatc agggggataac gcaggaaaga acatgtgagc    5100
aaaaggccag caaaaggcca ggaaccgtaa aaaggccgcg ttgctggcgt ttttccatag    5160
gctccgcccc cctgacgagc atcacaaaaa tcgacgctca agtcagaggt ggcgaaaccc    5220
gacaggacta taaagatacc aggcgtttcc ccctggaagc tccctcgtgc gctctcctgt    5280
tccgaccctg ccgcttaccg gatacctgtc cgcctttctc ccttcgggaa gcgtggcgct    5340
ttctcatagc tcacgctgta ggtatctcag ttcggtgtag tcgttcgct ccaagctggg    5400 ctgtgtgcac gaaccccccg ttcagcccga ccgctgcgcc ttatccggta actatcgtct    5460
tgagtccaac ccggtaagac acgacttatc gccactggca gcagccactg gtaacaggat    5520
tagcagagcg aggtatgtag gcggtgctac agagttcttg aagtggtggc ctaactacgg    5580
ctacactaga aggacagtat ttggtatctg cgctctgctg aagccagtta ccttcggaaa    5640
aagagttggt agctcttgat ccggcaaaca aaccaccgct ggtagcggtg gtttttttgt    5700
ttgcaagcag cagattacgc gcagaaaaaa aggatctcaa gaagatcctt tgatcttttc    5760
tacggggtct gacgctcagt ggaacgaaaa ctca                                5794

<210> SEQ ID NO 3
<211> LENGTH: 14119
<212> TYPE: DNA
<213> ORGANISM: Artificial
<220> FEATURE:
<223> OTHER INFORMATION: Eukaryotic expression vector

<400> SEQUENCE: 3
cgttgtaaaa cgacggccag tgaattgtaa tacgactcac tatagggcga attgggtacc      60
gggccccccc tcgaagttta acatttaaa tctagaagct tcaatgtttt tagcaccctc     120
tgtgtggagg aaaataatgc agattattct aattagtgta atatctaacc acattaaaat     180
atattacata gtaaactaca ctccataatt ttataaattt gactccccag ggtaataaac     240
tagtctctag tctgctcacc ttcaactgta caataaagtc ttggttcttt tgaaatagac     300
ctcaaatgag acacctaaaa ttcaaagtgt ctttacattt aaagacacct acaggaaagc     360
aggtaaaaga gccaggttaa aaacaaattc taaaaccact tagctgcagt taaacatata     420
gtaaagatgc actaaagttt cttactctgt aaatcccttc cacttcagga atattccac      480 tttcccattc actacacgtc gatctagtac ttttccacg acaaattctt caggctctgc      540
ctcttcaact ttttttactct ttccattctg ttttttttccc atttttgct aaaataaaac     600
```

-continued

```
aaaagagaaa ttaagaaata ttcctcttga attttgagca catttcaag gctcaattgc      660
ttatattatt atcacattcg acataaattt ttacttctat atcccagggc agacaccttc      720
tggaaagatt aaaagtcaac agacaataaa ataaaagaat gctttatctt gttcatttag      780
ttcaaactta caacccacca ccaaaataat acaataaaaa aacactatct ggaaacagtt      840
atttttttcc agtctttttt tttgagacag ggtctcacac tcttgtcgcc caggctggag      900
tgcagtggcg tgatctcagc tcactgcaac ctccgcctcc ccaggttcaa gcagttctca      960
tgcctcagcc tccagagtag ctgggattat aggcggatgc caccatgccg gctaattttt     1020
ttttgtgttt ttattagaaa cagggtttca ccatgttgac caggctggtc tcaaactcct     1080
gacctgaagt gattcaccag cctgggcctc ccaaagtgct ggcattacag gcgtgagcca     1140
ctgcgcccgg ccctgtagtc ttaaaagacc aagtttacta attttcactc attttaacaa     1200
cactgcaaca aacaactatg caggaagtac ctaaagggtg atccagagaa gcaagtagta     1260
gtgacaggtc ttaggtgaac ctatgacaga ccttgtatcc accccagat ggtaaaagcc      1320
ccagccccct tctcaattca aatattaatg tcaaaagcat caatgataca gagaaaagat     1380
aaatgcagaa tgaaaacatg gttcaaaatc ctgataccaa ctgcagggtc aactatagag     1440
accactagga ggttcaatta aaggacaaga ttattttttcc ataatctctg tagataatat    1500
ttcctaccac ttagaacaaa actataaagc tatcacttca agagaccaac attacaaatt    1560
tattttaatt ccctaaggtg aaaaaaatcc ttccttcctg gtttctcaag agaaagtcta    1620
tactggtaac caaattcact ttaaacaggc attttctttg gtatgacact atttaagaga    1680
agcaggaaac caacgtgaac cagctctttc caatggctca agatttccta tgagaggact    1740
aaaaatgggg aaaattttta tgagaggatt aaaaatgggg gaaaaaaaac cctgaaatgg    1800
ttaatcagaa gatcctatgg gctgagaagg aatccatctt aacatttcat cttaaagcaa    1860
atgctattgc cggggcagt ggctcatgcc tgtaatccca gcactttggg aggccgaggt    1920
gggcagatca tctgaggtca ggagtttgag accagcctga ccaacatgga gaaacccgt    1980
ttctactaaa aatacaaaat tagccaggca tagtggtgca tgcctgtaat cccagctact    2040
tgggaggctg aggcaggaga actgcttgaa cccaggaggc ttaagttgcg gtgagccaag    2100
atcacgccat tgcactctag cctggacaac aagagaaaaa ctctgtctca aaaaaacaca    2160
aaaacaaaaa acccaaatac tatttaaaaa agataaacct taattgctca atcattaaag    2220
ccatcccaca agtaaagcag caagcagaaa aaagttaaga acacctcaag gctacagaag    2280
gacatttcaa gctatgcagg catatgaagt gtgcagacag atatgtaaga aaggcctcaa    2340
gactgcaaaa gggcatttca agctatgcaa gcataggt aacacataca cacacacaaa    2400
ataaaatccc ctgaaataca aaacatgca gcaaacacct gacgttttg gataccattt    2460
ctaagtcagg tgttatgatt ctcattagtc aagatacttg agtactgggc ccaaacagct    2520
ttctgccact gtacagtaca agaaggtagg aataatggtg ggaggagcaa agacaaactg    2580
taatagacag aagtgtatca gatacctata ctacatgaaa aacaaaacag ctactgccac    2640
aaagggagaa ggctaacaaa ataaagtcaa caataaatac agaaaatgaa aaggatacac    2700
actaaggttt acaaaaaaaa aaaggcagac aaaatgccat acagtattca ttcactacta    2760
tggcattcat aagctagttt caatgctca ctattttctt ttatagtata tatttgcctt    2820
aacccagcac ttttttccaa aagtggatga gtcaaaataa atttcccatt atttaagtga    2880
aattaacagc acacatatct cacaacacta atgaattttt aaaatggaaa gttaagaact    2940
tttaaagtgg ccaacctgtg atccttcaca aaataaacta aatacaataa cagaccccaa    3000
```

-continued

```
aggctatcaa ttgcgtgcaa aaacaacttc tgttttccag ggtaaacaga atctaatgca    3060
gaatctaatg cagggtaaac agacttaatg cagaatctaa tgatggcaca aattaaaaat    3120
cactaacgtg cccttttag tgtgaaaccc agagagagca catacaagcc aaaaacaaat    3180
gctttatttt acctaggaga cattaacatt caccttacg tgtttaagat taatgcaatg    3240
ttaaatattg tgaaaactgt aactttgaat ttcatgattt ttatgtgaat attccagggt    3300
ttaaaaaaac ttgtaacatg acatggctga ataagataaa aaaaaatct agccttttct    3360
cccttctggc tcatatttgc gatttcgatc attttgttta aaaacaaaa cactgcaatg    3420
aattaaactt aatattcttc tatgttttag agtaagttaa aacaagataa agtgaccaaa    3480
gtaatttgaa agattcaatg acttttgctc caacctaggt gcacaaggta ccttgttctt    3540
taaattgggc tttaatgaaa atacttctcc agaattctgg ggatttaaga aaaattatgc    3600
caaccaacaa gggctttacc attttatgta acatttttca acgctgcaaa aatgtgtgta    3660
tttctatttg aagataaaaa tcctcagcaa aatccacatt gcactgtcct tcaaagatta    3720
gccttctttg aactagttaa gacactatta agccaagcca gtatctccct gtaatgaatt    3780
cgttttctc ttaattttcc cctgtaattt acactgggag agctgggaaa tatgtggatg    3840
taaatttctc agccacagag atgcaaagtt atactgtggg gaaaaaaaac ttgagttaaa    3900
tccttacata ttttaggttt tcattaactt accaatgtag ttttgttgga ggccatttt    3960
tttattgcag acttgaagag ctattactag aaaaatgcat gacagttaag gtaagtttgc    4020
atgacacaaa aaaggtaact aaatacaaat tctgtttgga ttccaacccc caagtagaga    4080
gcgcacactt tcaaacgtga atacaaatcc agagtagatc tgcgctccta cctacattgc    4140
ttatgatgta cttaagtacg tgtcctaacc atgtgagtct agaaagactt tactggggat    4200
cctggtacct aaaacagctt cacatggctt aaaatagggg accaatgtct tttccaatct    4260
aagtcccatt tataataaag tccatgttcc atttttaaag acaatccctt tcggtttaaa    4320
accaggcacg attacccaaa caactcacaa cggtaaagca ctgtgaatct tctctgttct    4380
gcaatcccaa cttggtttct gctcagaaac cctccctctt tccaatcggt aattaaataa    4440
caaaaggaaa aaacttaaga tgcttcaacc ccgtttcgtg acactttgaa aaaagaatca    4500
cctcttgcaa acaccgctc ccgaccccg ccgctgaagc ccggcgtcca gaggcctaag    4560
cgcgggtgcc cgccccacc cgggagcgcg ggcctcgtgg tcagcgcatc cgcggggaga    4620
aacaaaggcc gcggcacggg ggctcaaggg cactgcgcca caccgcacgc gcctaccccc    4680
gcgcggccac gttaactggc ggtcgccgca gcctcgggac agccggccgc gcgccgccag    4740
gctcgcggac gcgggaccac gcgccgcccct ccggggaggcc caagtctcga cccagccccg    4800
cgtggcgctg ggggagggg cgcctccgcc ggaacgcggg tggggagggg gaggggaaa    4860
tgcgctttgt ctcgaaatgg ggcaaccgtc gccacagctc cctaccccct cgagggcaga    4920
gcagtccccc cactaactac cgggctggcc gcgcgccagg ccagccgcga ggccaccgcc    4980
cgaccctcca ctccttcccg cagctcccgg cgcggggtcc ggcgagaagg ggaggggagg    5040
ggagcggaga accgggcccc cggacgcgt gtggcatctg aagcaccacc agcgagcgag    5100
agctagagag aaggaaagcc accgacttca ccgcctccga gctgctccgg gtcgcgggtc    5160
tgcagcgtct ccggccctcc gcgcctacag ctcaagccac atccgaaggg ggagggagcc    5220
gggagctgcg cgcggggccg ccggggggag ggtggcacc gcccacgccg gcggccacg    5280
aagggcgggg cagcgggcgc gcgcgcggcg ggggagggg ccggcgccgc gcccgctggg    5340
```

-continued

```
aattggggcc ctaggggag ggcggaggcg ccgacgaccg cggcacttac cgttcgcggc      5400
gtggcgcccg gtggtcccca aggggaggga aggggaggc ggggcgagga cagtgaccgg      5460
agtctcctca gcggtggctt ttctgcttgg cagcctcagc ggctggcgcc aaaaccggac      5520
tccgcccact tcctcgcccg ccggtgcgag ggtgtggaat cctccagacg ctggggagg      5580 gggagttggg agcttaaaaa ctagtacccc tttgggacca ctttcagcag cgaactctcc      5640
tgtacaccag gggtcagttc cacagacgcg ggccaggggt gggtcattgc ggcgtgaaca      5700
ataatttgac tagaagttga ttcgggtgtt tccggaaggg gccgagtcaa tccgccgagt      5760
tggggcacgg aaaacaaaaa gggaaggcta ctaagatttt tctggcgggg gttatcattg      5820
gcgtaactgc agggaccacc tcccgggttg aggggctgg atctccaggc tgcggattaa      5880
gcccctcccg tcggcgttaa tttcaaactg cgcgacgttt ctcacctgcc ttcgccaagg      5940
caggggccgg gaccctattc caagaggtag taactagcag gactctagcc ttccgcaatt      6000
cattgagcgc atttacggaa gtaacgtcgg gtactgtctc tggccgcaag ggtgggagga      6060
gtacgcattt ggcgtaaggt ggggcgtaga gccttcccgc cattggcggc ggatagggcg      6120
tttacgcgac ggcctgacgt agcggaagac gcgttagtgg gggggaaggt tctagaaaag      6180
cggcggcagc ggctctagcg gcagtagcag cagcgccggg tcccgtgcgg aggtgctcct      6240
cgcagagttg tttctcgagc agcggcagtt ctcactacag cgccaggacg agtccggttc      6300
gtgttcgtcc gcggagatct ctctcatctc gctcggctgc gggaaatcgg gctgaagcga      6360
ctgagtccgc gatggaggta acgggtttga aatcaatgag ttattgaaaa gggcatggcg      6420
aggccgttgg cgcctcagtg gaagtcggcc agccgcctcc gtgggagaga ggcaggaaat      6480
cggaccaatt cagtagcagt ggggcttaag gtttatgaac ggggtcttga gcggaggcct      6540
gagcgtacaa acagcttccc caccctcagc ctcccggcgc catttccctt cactggggt      6600 ggggatggg gagctttcac atggcggacg ctgccccgct ggggtgaaag tggggcgcgg      6660
aggcgggaat tcttattccc tttctaaagc acgctgcttc gggggccacg gcgtctcctc      6720
ggcgagcgtt tcggcgggca gcaggtcctc gtgagcgagg ctgcggagct tcccctcccc      6780
ctctctcccg ggaaccgatt tggcggccgc catttcatg gctcgccttc ctctcagcgt      6840
tttccttata actcttttat tttcttagtg tgctttctct atcaagaagt agaagtggtt      6900 aactatttt ttttcttct cgggctgttt tcatatcgtt tcgaggtgga tttggagtgt      6960
tttgtgagct tggatcttta gagtcctgcg cacctcatta aaggcgctca gccttcccct      7020
cgatgaaatg gcgccattgc gttcggaagc cacaccgaag agcggggagg gggggtgctc      7080
cgggtttgcg ggcccggttt cagagaagat atcaccaccc agggcgtcgg gccgggttca      7140
atgcgagccg taggacaaag aaaccatttt atgttttcc tgtctttttt ttcctttgag      7200
taacggtttt atctgggtct gcagtcagta aaacgacaga tgaaccgcgg caaaataaac      7260
ataaattgga agccatcggc cacgagggc agggacgaag gtggttttct gggcggggga      7320
gggatattcg cgtcagaatc ctttactgtt cttaaggatt ccgtttaagt tgtagagctg      7380
actcatttta agtaatgttg ttactgagaa gtttaacct tacgggacag atccatggac      7440
ctttatagat gattacgagg aaagtgaaat aacgattttg tccttagtta tacttcgatt      7500
aaaacatggc ttcagaggct ccttcctgta atgcgtatgg attgatgtgc aaaactgttt      7560
tgggcctggg ccgctctgta tttgaacttt gttactttc tcatttgtt tgcaatcttg      7620 gttgaacatt acattgataa gcataaggtc tcaagcgaag ggggtctacc tggttatttt      7680
tctttgaccc taagcacgtt tataaaataa cattgtttaa aatcgatagt ggacatcggg      7740
```

-continued

```
taagtttgga taaattgtga ggtaagtaat gagttttttgc ttttttgttag tgatttgtaa    7800 aacttgttat aaatgtacat tatccgtaat ttcagtttag agataaccta tgtgctgacg    7860
acaattaaga ataaaaacta gctgaaaaaa tgaaaataac tatcgtgaca agtaaccatt    7920
tcaaaagact gctttgtgtc tcataggagc tagtttgatc atttcagtta attttttctt    7980 taattttttac gagtcatgaa aactacagga aaaaaaatct gaactgggtt ttaccactac    8040 ttttttaggag ttgggagcat gcgaatggag ggagagctcc gtagaactgg gatgagagca    8100
gcaattaatg ctgcttgcta ggaacaaaaa ataattgatt gaaaattacg tgtgactttt    8160
tagtttgcat tatgcgtttg tagcagttgg tcctggatat cactttctct cgtttgaggt    8220
tttttaacct agttaacttt taagacaggt ttccttaaca ttcataagtg cccagaatac    8280
agctgtgtag tacagcatat aaagatttca gctctgaggt ttttcctatt gacttggaaa    8340
attgttttgt gcctgtcgct tgccacatgg ccaatcaagt aagcttatcg ataccggtgg    8400
agctcaagct tcgaattctg cagtcgacgg taccgcgggc ccgggatcta tgttacttgg    8460
cagaggccgc atggaaagtc cctggacgtg ggacatctga ttaatacgtg aggaggtcag    8520
ccatgttctt tttggcaaag gactacggtc attggacgtt tgattggcat gggatagggt    8580
cagccagagt taacagtgtt cttttggcaa agggatacgt ggaaagtccc gggccattta    8640
cagtaaactg atacggggac aaagcacagc catatttagt catgtattgc ttggcagagg    8700
gtctatggaa agtccctgga cgtgggacgt ctgattaata tgaaagaagg tcagccagag    8760
gtagctgtgt cctttttggc aaagggatac ggttatggga cgtttgattg gactgggata    8820
gggtcagcca gagttaacag tgttcttttg gcaaaggaaa cgtggaaagt cccgggccat    8880
ttacagtaaa ctgatactgg gacaaagtac acccatattt agtcatgttc ttttttggcaa    8940 agagcatctg gaaagtcccg ggcagcatta tagtcacttg gcagagggaa agggtcactc    9000
agagttaagt acatctttcc agggccaata ttccagtaaa ttacacttag ttttatgcaa    9060
atcagccaca aagggggattt tcccggtcaa ttatgacttt ttccttagtc atgcggtatc    9120
caattactgc caaattggca gtacatacta ggtgattcac tgacatttgg ccgtcctctg    9180
gaaagtccct ggaaaccgct caagtactgt atcatggtga ctttgcattt ttggagagca    9240
cgccccactc caccattggt ccacgtaccc tatgggggag tggtttatga gtatataagg    9300
ggctccggtt tagaagccgg gcagagcgga attgatccac cggtcgccac catggtgagc    9360
aagggcgagg agctgttcac cggggtggtg cccatcctgg tcgagctgga cggcgacgta    9420
aacggccaca gttcagcgt gtccggcgag ggcgagggcg atgccaccta cggcaagctg    9480
accctgaagt tcatctgcac caccggcaag ctgcccgtgc cctggcccac cctcgtgacc    9540
accctgacct acggcgtgca gtgcttcagc cgctaccccg accacatgaa gcagcacgac    9600
ttcttcaagt ccgccatgcc cgaaggctac gtccaggagc gcaccatctt cttcaaggac    9660
gacggcaact acaagacccg cgccgaggtg aagttcgagg gcgacaccct ggtgaaccgc    9720
atcgagctga agggcatcga cttcaaggag gacggcaaca tcctggggca caagctggag    9780
tacaactaca acagccacaa cgtctatatc atggccgaca agcagaagaa cggcatcaag    9840
gtgaacttca agatccgcca caacatcgag gacggcagcg tgcagctcgc cgaccactac    9900
cagcagaaca cccccatcgg cgacggcccc gtgctgctgc ccgacaacca ctacctgagc    9960
acccagtccg ccctgagcaa agaccccaac gagaagcgcg atcacatggt cctgctggag   10020
ttcgtgaccg ccgccgggat cactctcggc atggacgagc tgtacaagta aagcggccgc   10080
```

```
gactctagat cataatcagc cataccacat ttgtagaggt tttacttgct ttaaaaaacc   10140
tcccacacct cccctgaac ctgaaacata aatgaatgc aattgttgtt gttaacttgt    10200
ttattgcagc ttataatggt tacaaataaa gcaatagcat cacaaatttc acaaataaag   10260
catttttttc actgcattct agttgtggtt tgtccaaact catcaatgta tcttaactag   10320
agtcgacctg caggcatgca agcttaccgg tggcgcgcgc gccaattgtt aattaagatc   10380
tggcccaatg ggccgtacga attccttagg ctaccgggta ggggaggcgc ttttcccaag   10440
gcagtctgga gcatgcgctt tagcagcccc gctgggcact tggcgctaca caagtggcct   10500
ctggcctcgc acacattcca catccaccgg ccggtaggcg ccaaccggct ccgttctttg   10560
gtggcccctt cgcgccacct tctactcctc ccctagtcag gaagttcccc cccgccccgc   10620
agctcgcgtc gtgcaggacg tgacaaatgg aagtagcacg tctcactagt ctcgtgcaga   10680
tggacagcac cgctgagcaa tggaagcggg taggcctttg gggcagcggc caatagcagc   10740
tttgctcctt cgctttctgg gctcagaggc tgggaagggg tgggtccggg ggcgggctca   10800
ggggcgggct caggggcggg gcgggcgccc gaaggtcctc cggaggcccg gcattctgca   10860
cgcttcaaaa gcgcacgtct gccgcgctgt tctcctcttc ctcatctccg gccttttcga   10920
ccagcttacc atgaccgagt acaagcccac ggtgcgcctc gccacccgcg acgacgtccc   10980
cagggccgta cgcaccctcg ccgcgcgtt cgccgactac cccgccacgc gccacaccgt   11040
cgatccggac cgccacatcg agcgggtcac cgagctgcaa gaactcttcc tcacgcgcgt   11100
cgggctcgac atcggcaagg tgtgggtcgc ggacgacggc gccgcggtgg cggtctggac   11160
cacgccggag agcgtcgaag cggggcggt gttcgccgag atcggcccgc gcatggccga   11220
gttgagcggt tccggctgg ccgcgcagca acagatggaa ggcctcctgg cgccgcaccg   11280
gcccaaggag cccgcgtggt tcctggccac cgtcggcgtc tcgcccgacc accagggcaa   11340
gggtctgggc agcgccgtcg tgctccccgg agtggaggcg gccgagcgcg ccggggtgcc   11400
cgccttcctg gagacctccg cgccccgcaa cctccccttc tacgagcggc tcggcttcac   11460
cgtcaccgcc gacgtcgagg tgcccgaagg accgcgcacc tggtgcatga cccgcaagcc   11520
cggtgcctga cgcccgcccc acgacccgca gcgcccgacc gaaaggagcg cacgaccca   11580 tgcatcgtag acgaaatgac cgaccaagcg acgcccaacc tgccatcacg agatttcgat   11640
tccaccgccg ccttctatga aaggttgggc ttcggaatcg ttttccggga cgccggctgg   11700
atgatcctcc agcgcgggga tctcatgctg gagttcttcg cccacccctag ggggaggcta   11760 actgaaacac ggaaggagac aataccggaa ggaacccgcg ctatgacggc aataaaaaga   11820
cagaataaaa cgcacggtgt tgggtcgttt gttcataaac gcggggttcg gtcccagggc   11880
tggcactctg tcgataccc accgagaccc cattggggcc aatacgcccg cgtttcttcc   11940 tttttcccccac ccccaccccc aagttcgggt gaaggcccag ggctcgcagc caacgtcggg   12000
gcggcaggcc cccagctttt gttccccttta gtgagggtta atttcgagct tggcgtaatc   12060
atggtcatag ctgtttcctg tgtgaaattg ttatccgctc acaattccac acaacatacg   12120
agccggaagc ataaagtgta aagcctgggg tgcctaatga gtgagctaac tcacattaat   12180
tgcgttgcgc tcactgcccg ctttccagtc gggaaacctg tcgtgccagc atcgcgagca   12240
cttttcgggg aaatgtgcgc ggaaccccta tttgtttatt tttctaaata cattcaaata   12300
tgtatccgct catgagacaa taaccctgat aaatgcttca ataatattga aaaggaaga   12360 gtatgagtat tcaacatttc cgtgtcgccc ttattccctt ttttgcggca ttttgccttc   12420 ctgttttgc tcacccagaa acgctggtga agtaaaaga tgctgaagat cagttgggtg   12480
```

```
cacgagtggg ttacatcgaa ctggatctca acagcggtaa gatccttgag agttttcgcc   12540
ccgaagaacg ttttccaatg atgagcactt ttaaagttct gctatgtggc gcggtattat   12600
cccgtattga cgccgggcaa gagcaactcg gtcgccgcat acactattct cagaatgact   12660
tggttgagta ctcaccagtc acagaaaagc atcttacgga tggcatgaca gtaagagaat   12720
tatgcagtgc tgccataacc atgagtgata acactgcggc caacttactt ctgacaacga   12780
tcggaggacc gaaggagcta accgcttttt tgcacaacat gggggatcat gtaactcgcc   12840
ttgatcgttg ggaaccggag ctgaatgaag ccataccaaa cgacgagcgt gacaccacga   12900
tgcctgtagc aatggcaaca acgttgcgca aactattaac tggcgaacta cttactctag   12960
cttcccggca acaattaata gactggatgg aggcggataa agttgcagga ccacttctgc   13020
gctcggccct tccggctggc tggtttattg ctgataaatc tggagccggt gagcgtgggt   13080
ctcgcggtat cattgcagca ctggggccag atggtaagcc ctcccgtatc gtagttatct   13140
acacgacggg gagtcaggca actatggatg aacgaaatag acagatcgct gagataggtg   13200
cctcactgat taagcattgg taactgtcag actcgcgaca ctgcattaat gaatcggcca   13260
acgcgcgggg agaggcggtt tgcgtattgg gcgctcttcc gcttcctcgc tcactgactc   13320
gctgcgctcg tcgttcggc tgcggcgagc ggtatcagct cactcaaagg cggtaatacg   13380
gttatccaca gaatcagggg ataacgcagg aaagaacatg tgagcaaaag gccagcaaaa   13440
ggccaggaac cgtaaaaagg ccgcgttgct ggcgtttttc cataggctcc gcccccctga   13500
cgagcatcac aaaaatcgac gctcaagtca gaggtggcga aacccgacag gactataaag   13560
ataccaggcg tttccccctg gaagctccct cgtgcgctct cctgttccga ccctgccgct   13620
taccggatac ctgtccgcct ttctcccttc gggaagcgtg cgctttctc atagctcacg   13680 ctgtaggtat ctcagttcgg tgtaggtcgt tcgctccaag ctgggctgtg tgcacgaacc   13740
ccccgttcag cccgaccgct cgccttatc cggtaactat cgtcttgagt ccaacccggt   13800
aagacacgac ttatcgccac tggcagcagc cactggtaac aggattagca gagcgaggta   13860
tgtaggcggt gctacagagt tcttgaagtg gtggcctaac tacggctaca ctagaaggac   13920
agtatttggt atctgcgctc tgctgaagcc agttaccttc ggaaaaagag ttggtagctc   13980
ttgatccggc aaacaaacca ccgctggtag cggtggtttt tttgtttgca agcagcagat   14040
tacgcgcaga aaaaaggat ctcaagaaga tcctttgatc ttttctacgg ggtctgacgc   14100
tcagtggaac gaaaactca                                                14119
```

```
<210> SEQ ID NO 4
<211> LENGTH: 7383
<212> TYPE: DNA
<213> ORGANISM: Artificial
<220> FEATURE:
<223> OTHER INFORMATION: Eukaryotic expression vector

<400> SEQUENCE: 4
cgttgtaaaa cgacggccag tgaattgtaa tacgactcac tatagggcga attgggtacc     60
gggccccccc tcgaagttta acatttcta gcgctaccgg actcagatcc cctccgcgcc    120
tacagctcaa gccacatccg aaggggagg gagccgggag ctgcgcgcgg ggccgccggg    180
ggagggggtg gcaccgccca cgccgggcgg ccacgaaggg cggggcagcg ggcgcgcgcg    240
cggcgggggg aggggccggc gccgcgcccg ctgggaattg ggccctagg ggagggcgg    300 aggcgccgac gaccgcggca cttaccgttc gcggcgtggc gccggtggt ccccaagggg    360
```

```
agggaagggg gaggcgggc gaggacagtg accggagtct cctcagcggt ggcttttctg    420
cttggcagcc tcagcggctg gcgccaaaac cggactccgc ccacttcctc gcccgccggt    480
gcgagggtgt ggaatcctcc agacgctggg ggagggggag ttgggagctt aaaaactagt    540
acccctttgg gaccactttc agcagcgaac tctcctgtac accaggggtc agttccacag    600
acgcgggcca ggggtgggtc attgcggcgt aacaataat ttgactagaa gttgattcgg     660
gtgtttccgg aagggggccga gtcaatccgc cgagttgggg cacggaaaac aaaaagggaa   720
ggctactaag attttctgg cggggttat cattggcgta actgcaggga ccacctcccg      780
ggttgagggg ctggatctc caggctgcgg attaagcccc tcccgtcggc gttaatttca     840
aactgcgcga cgtttctcac ctgccttcgc caaggcaggg gccgggaccc tattccaaga    900
ggtagtaact agcaggactc tagccttccg caattcattg agcgcattta cggaagtaac    960
gtcgggtact gtctctggcc gcaagggtgg gaggagtacg catttggcgt aaggtggggc   1020
gtagagcctt cccgccattg gcggcggata gggcgtttac gcgacggcct gacgtagcgg   1080
aagacgcgtt agtgggggg aaggttctag aaaagcggcg gcagcggctc tagcggcagt    1140
agcagcagcg ccgggtcccg tgcggagtg ctcctcgcag agttgtttct cgagcagcgg    1200
cagttctcac tacagcgcca ggacgagtcc ggttcgtgtt cgtccgcgga gatctctctc   1260
atctcgctcg gctgcgggaa atcgggctga agcgactgag tccgcgatgg aggtaacggg   1320
tttgaaatca atgagttatt gaaaagggca tggcgaggcc gttggcgcct cagtggaagt   1380
cggccagccg cctccgtggg agagaggcag gaaatcggac caattcagta gcagtggggc   1440
ttaaggttta tgaacggggt cttgagcgga ggcctgagcg tacaaacagc ttccccaccc   1500
tcagcctccc ggcgccattt ccttcactg ggggtgggg atgggagct ttcacatggc      1560
ggacgctgcc ccgctggggt gaaagtgggg cgcggaggcg ggaattctta ttcccttct    1620
aaagcacgct gcttcggggg ccacggcgtc tcctcgggat ctcgagctca agcttcgaat   1680
tctgcagtcg acggtaccgc gggcccggga tctatgttac ttggcagagg ccgcatggaa   1740
agtccctgga cgtgggacat ctgattaata cgtgaggagg tcagccatgt tcttttggc    1800
aaaggactac ggtcattgga cgtttgattg gcatgggata gggtcagcca gagttaacag   1860
tgttctttg gcaaagggat acgtggaaag tcccgggcca tttacagtaa actgatacgg    1920
ggacaaagca cagccatatt tagtcatgta ttgcttggca gagggtctat ggaaagtccc   1980
tggacgtggg acgtctgatt aatatgaaag aaggtcagcc agaggtagct gtgtcctttt   2040
tggcaaaggg atacggttat gggacgtttg attggactgg gatagggtca gccagagtta   2100
acagtgttct tttggcaaag gaaacgtgga aagtcccggg ccatttacag taaactgata   2160
ctgggacaaa gtacacccat atttagtcat gttcttttg gcaaagagca tctggaaagt    2220
cccgggcagc attatagtca cttggcagag ggaaagggtc actcagagtt aagtacatct   2280
ttccagggcc aatattccag taaattacac ttagtttat gcaaatcagc cacaaagggg    2340
attttcccgg tcaattatga ctttttcctt agtcatgcgg tatccaatta ctgccaaatt   2400
ggcagtacat actaggtgat tcactgacat ttggccgtcc tctggaaagt ccctggaaac   2460
cgctcaagta ctgtatcatg gtgactttgc attttggag agcacgcccc actccaccat   2520
tggtccacgt accctatggg ggagtggttt atgagtatat aaggggctcc ggtttagaag   2580
ccgggcagag cggaattgat ccaccggtcg ccaccatggt gagcaagggc gaggagctgt   2640
tcaccggggg ggtgcccatc ctggtcgagc tggacgcga cgtaaacggc cacaagttca    2700
gcgtgtccgg cgagggcgag ggcgatgcca cctacggcaa gctgaccctg aagttcatct   2760
```

```
gcaccaccgg caagctgccc gtgccctggc ccaccctcgt gaccaccctg acctacggcg    2820
tgcagtgctt cagccgctac cccgaccaca tgaagcagca cgacttcttc aagtccgcca    2880
tgcccgaagg ctacgtccag gagcgcacca tcttcttcaa ggacgacggc aactacaaga    2940
cccgcgccga ggtgaagttc gagggcgaca ccctggtgaa ccgcatcgag ctgaagggca    3000
tcgacttcaa ggaggacggc aacatcctgg gcacaagct ggagtacaac tacaacagcc    3060
acaacgtcta tatcatggcc gacaagcaga agaacggcat caaggtgaac ttcaagatcc    3120
gccacaacat cgaggacggc agcgtgcagc tcgccgacca ctaccagcag aacacccca    3180
tcggcgacgg ccccgtgctg ctgcccgaca accactacct gagcacccag tccgccctga    3240
gcaaagaccc caacgagaag cgcgatcaca tggtcctgct ggagttcgtg accgccgccg    3300
ggatcactct cggcatggac gagctgtaca gtaaagcgg ccgcgactct agatcataat    3360
cagccatacc acatttgtag aggttttact tgctttaaaa aacctcccac acctcccct    3420
gaacctgaaa cataaaatga atgcaattgt tgttgttaac ttgtttattg cagcttataa    3480
tggttacaaa taaagcaata gcatcacaaa tttcacaaat aaagcatttt tttcactgca    3540
ttctagttgt ggtttgtcca aactcatcaa tgtatcttaa ctagagtcga cctgcaggca    3600
tgcaagctta ccggtggcgc gcgcgccaat tgttaattaa gatctggccc aatgggccgt    3660
acgaattcct taggctaccg ggtagggag gcgcttttcc caaggcagtc tggagcatgc    3720
gctttagcag ccccgctggg cacttggcgc tacacaagtg gcctctggcc tcgcacacat    3780
tccacatcca ccggccggta ggcgccaacc ggctccgttc tttggtggcc ccttcgcgcc    3840
accttctact cctcccctag tcaggaagtt ccccccgcc ccgcagctcg cgtcgtgcag    3900
gacgtgacaa atgaagtag cacgtctcac tagtctcgtg cagatggaca gcaccgctga    3960
gcaatggaag cgggtaggcc tttggggcag cggccaatag cagctttgct ccttcgcttt    4020
ctgggctcag aggctgggaa ggggtgggtc cggggcggg ctcaggggcg gctcagggg    4080
cggggcgggc gcccgaaggt cctccggagg cccggcattc tgcacgcttc aaaagcgcac    4140
gtctgccgcg ctgttctcct cttcctcatc tccgggcctt tcgaccagct taccatgacc    4200
gagtacaagc ccacggtgcg cctcgccacc cgcgacgacg tccccagggc cgtacgcacc    4260
ctcgccgccg cgttcgccga ctaccccgcc acgcgccaca ccgtcgatcc ggaccgccac    4320
atcgagcggg tcaccgagct gcaagaactc ttcctcacgc gcgtcgggct cgacatcggc    4380
aaggtgtggg tcgcggacga cggcgccgcg gtggcggtct ggaccacgcc ggagagcgtc    4440
gaagcggggg cggtgttcgc cgagatcggc ccgcgcatgg ccgagttgag cggttcccgg    4500
ctggccgcgc agcaacagat ggaaggcctc ctggcgccgc accggcccaa ggagcccgcg    4560
tggttcctgg ccaccgtcgg cgtctcgccc gaccaccagg caagggtct gggcagcgcc    4620
gtcgtgctcc ccggagtgga ggcggccgag gcgccggg tgcccgcctt cctggagacc    4680
tccgcgcccc gcaacctccc cttctacgag cggctcggct tcaccgtcac cgccgacgtc    4740
gaggtgcccg aaggaccgcg cacctggtgc atgaccgca gcccggtgc ctgacgcccg    4800
ccccacgacc cgcagcgccc gaccgaaagg agcgcacgac cccatgcatc gtagacgaaa    4860
tgaccgacca agcgacgccc aacctgccat cacgagattt cgattccacc gccgccttct    4920
atgaaaggtt gggcttcgga atcgttttcc gggacgccgg ctggatgatc ctccagcgcg    4980
gggatctcat gctggagttc ttcgcccacc ctaggggag gctaactgaa acacggaagg    5040
agacaatacc ggaaggaacc cgcgctatga cggcaataaa aagacagaat aaaacgcacg    5100
```

-continued

```
gtgttgggtc gtttgttcat aaacgcgggg ttcggtccca gggctggcac tctgtcgata    5160
ccccaccgag accccattgg ggccaatacg cccgcgtttc ttccttttcc ccaccccacc    5220
ccccaagttc gggtgaaggc ccagggctcg cagccaacgt cggggcggca ggccccccagc   5280 ttttgttccc tttagtgagg gttaatttcg agcttggcgt aatcatggtc atagctgttt    5340
cctgtgtgaa attgttatcc gctcacaatt ccacacaaca tacgagccgg aagcataaag    5400
tgtaaagcct ggggtgccta atgagtgagc taactcacat taattgcgtt gcgctcactg    5460
cccgctttcc agtcgggaaa cctgtcgtgc cagcatcgcg agcacttttc ggggaaatgt    5520
gcgcggaacc cctatttgtt tattttttcta atacattca aatatgtatc cgctcatgag    5580
acaataaccc tgataaatgc ttcaataata ttgaaaaagg aagagtatga gtattcaaca    5640
tttccgtgtc gcccttattc cctttttttgc ggcattttgc cttcctgttt ttgctcaccc    5700
agaaacgctg gtgaaagtaa aagatgctga agatcagttg ggtgcacgag tgggttacat    5760
cgaactggat ctcaacagcg gtaagatcct tgagagtttt cgccccgaag aacgttttcc    5820
aatgatgagc acttttaaag ttctgctatg tggcgcggta ttatcccgta ttgacgccgg    5880
gcaagagcaa ctcggtcgcc gcatacacta ttctcagaat gacttggttg agtactcacc    5940
agtcacagaa aagcatctta cggatggcat gacagtaaga gaattatgca gtgctgccat    6000
aaccatgagt gataacactg cggccaactt acttctgaca acgatcggag gaccgaagga    6060
gctaaccgct tttttgcaca acatggggga tcatgtaact cgccttgatc gttgggaacc    6120
ggagctgaat gaagccatac caaacgacga gcgtgacacc acgatgcctg tagcaatggc    6180
aacaacgttg cgcaaactat taactggcga actacttact ctagcttccc ggcaacaatt    6240
aatagactgg atggaggcgg ataaagttgc aggaccactt ctgcgctcgg cccttccggc    6300
tggctggttt attgctgata atctggagc cggtgagcgt gggtctcgcg gtatcattgc     6360
agcactgggg ccagatggta agccctcccg tatcgtagtt atctacacga cggggagtca    6420
ggcaactatg gatgaacgaa atagacagat cgctgagata ggtgcctcac tgattaagca    6480
ttggtaactg tcagactcgc gacactgcat taatgaatcg ccaacgcgc ggggagaggc     6540 ggtttgcgta ttgggcgctc ttccgcttcc tcgctcactg actcgctgcg ctcggtcgtt    6600
cggctgcggc gagcggtatc agctcactca aaggcggtaa tacggttatc cacagaatca    6660
ggggataacg caggaaagaa catgtgagca aaaggccagc aaaaggccag gaaccgtaaa    6720
aaggccgcgt tgctggcgtt tttccatagg ctccgccccc ctgacgagca tcacaaaaat    6780
cgacgctcaa gtcagaggtg gcgaaacccg acaggactat aaagatacca ggcgtttccc    6840
cctggaagct ccctcgtgcg ctctcctgtt ccgaccctgc cgcttaccgg atacctgtcc    6900
gcctttctcc cttcgggaag cgtggcgctt tctcatagct cacgctgtag gtatctcagt    6960
tcggtgtagg tcgttcgctc caagctgggc tgtgtgcacg aacccccegt tcagcccgac    7020 cgctgcgcct tatccggtaa ctatcgtctt gagtccaacc cggtaagaca cgacttatcg    7080
ccactggcag cagccactgg taacaggatt agcagagcga ggtatgtagg cggtgctaca    7140
gagttcttga agtggtggcc taactacggc tacactagaa ggacagtatt tggtatctgc    7200
gctctgctga agccagttac cttcggaaaa agagttggta gctcttgatc cggcaaacaa    7260
accaccgctg gtagcggtgg tttttttgtt tgcaagcagc agattacgcg cagaaaaaaa    7320
ggatctcaag aagatccttt gatctttttct acggggtctg acgctcagtg aacgaaaac    7380 tca                                                                  7383
```

```
<210> SEQ ID NO 5
<211> LENGTH: 33
<212> TYPE: DNA
<213> ORGANISM: Artificial
<220> FEATURE:
<223> OTHER INFORMATION: Oligonucleotide

<400> SEQUENCE: 5
tgtcgcgagt ctgacagtta ccaatgctta atc                              33

<210> SEQ ID NO 6
<211> LENGTH: 33
<212> TYPE: DNA
<213> ORGANISM: Artificial
<220> FEATURE:
<223> OTHER INFORMATION: Oligonucleotide

<400> SEQUENCE: 6
catcgcgagc acttttcggg gaaatgtgtg cgc                              33

<210> SEQ ID NO 7
<211> LENGTH: 33
<212> TYPE: DNA
<213> ORGANISM: Artificial
<220> FEATURE:
<223> OTHER INFORMATION: Oligonucleotide

<400> SEQUENCE: 7
tcgaagttta aacatttaaa tctagaagct tat                              33

<210> SEQ ID NO 8
<211> LENGTH: 38
<212> TYPE: DNA
<213> ORGANISM: Artificial
<220> FEATURE:
<223> OTHER INFORMATION: Oligonucleotide

<400> SEQUENCE: 8
ccggtatcga taagcttcta gatttaaatg tttaaact                         38

<210> SEQ ID NO 9
<211> LENGTH: 38
<212> TYPE: DNA
<213> ORGANISM: Artificial
<220> FEATURE:
<223> OTHER INFORMATION: Oligonucleotide

<400> SEQUENCE: 9
cgataccggt ggcgcgccaa ttgttaatta agatctgg                         38

<210> SEQ ID NO 10
<211> LENGTH: 38
<212> TYPE: DNA
<213> ORGANISM: Artificial
<220> FEATURE:
<223> OTHER INFORMATION: Oligonucleotide

<400> SEQUENCE: 10
cccattgggc cagatcttaa ttaacaattg gcgcgcca                         38

<210> SEQ ID NO 11
<211> LENGTH: 33
<212> TYPE: DNA
<213> ORGANISM: Artificial
<220> FEATURE:
<223> OTHER INFORMATION: Oligonucleotide
```

```
-continued

<400> SEQUENCE: 11
cccaatgggc cgtacgaatt ccttaggctc gag                              33

<210> SEQ ID NO 12
<211> LENGTH: 28
<212> TYPE: DNA
<213> ORGANISM: Artificial
<220> FEATURE:
<223> OTHER INFORMATION: Oligonucleotide

<400> SEQUENCE: 12
ggccctcgag cctaaggaat tcgtacgg                                    28
```